United States Patent
Plumptre et al.

(10) Patent No.: US 10,195,358 B2
(45) Date of Patent: Feb. 5, 2019

(54) DRUG DELIVERY DEVICE AND METHOD FOR ELIMINATING A CLEARANCE OF THE PISTON ROD FOR DRUG DELIVERY DEVICES

(71) Applicant: Sanofi-Aventis Deutschland GmbH, Frankfurt am Main (DE)

(72) Inventors: David Aubrey Plumptre, Worcestershire (GB); Paul Richard Draper, Worcestershire (GB); David Richard Mercer, Dorset (GB); Naceur Rekaya, Warwickshire (GB); Paul Griffin, Worcestershire (GB); Robert Veasey, Warwickshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 540 days.

(21) Appl. No.: 14/773,326

(22) PCT Filed: Mar. 10, 2014

(86) PCT No.: PCT/EP2014/054530
§ 371 (c)(1),
(2) Date: Sep. 5, 2015

(87) PCT Pub. No.: WO2014/139918
PCT Pub. Date: Sep. 18, 2014

(65) Prior Publication Data
US 2016/0015904 A1    Jan. 21, 2016

(30) Foreign Application Priority Data
Mar. 13, 2013 (EP) .................................... 13159053

(51) Int. Cl.
*A61M 31/00* (2006.01)
*A61M 5/00* (2006.01)
(Continued)

(52) U.S. Cl.
CPC ...... *A61M 5/31551* (2013.01); *A61M 5/3146* (2013.01); *A61M 5/31585* (2013.01);
(Continued)

(58) Field of Classification Search
CPC .... A61M 2005/31516; A61M 2207/00; A61M 2207/10; A61M 5/3146; A61M 5/31515; A61M 5/31551; A61M 5/31585
(Continued)

(56) References Cited

U.S. PATENT DOCUMENTS 533,575 A    2/1895  Wilkens
5,226,895 A   7/1993  Harris
(Continued)

FOREIGN PATENT DOCUMENTS

CN    102802703 A    11/2012
EP    0937471 A2    8/1999
(Continued)

OTHER PUBLICATIONS

Office Action issued in Chinese Patent Application No. 201480013614.1 dated Jun. 26, 2017.

*Primary Examiner* — Jason Flick
(74) *Attorney, Agent, or Firm* — Fish & Richardson P.C.

(57) ABSTRACT

The piston rod arrangement is in an assembled state before use and comprises a piston rod, a bung, which is intended to be driven by the piston rod, a body member, and a drive member. The piston rod is threadedly engaged with the body member, and the drive member is threadedly engaged with the piston rod and movable relative to the body member. A mechanism is provided defining unit steps of movement of the drive member and corresponding unit steps of movement of the piston rod. The piston rod is arranged in contact with the bung or at a distance from the bung that is less than a distance of one corresponding unit step of movement. When
(Continued)

the piston rod, the bung and the drive member are assembled in the body member, the piston rod is advanced with respect to the body member towards the bung, until the piston rod is stopped by the bung. The drive member is rotated until the piston rod begins to advance again and the drive member is then stopped, and the piston rod is fixed at or near the position obtained.

16 Claims, 14 Drawing Sheets

(51) Int. Cl.
*A61M 5/315* (2006.01)
*A61M 5/31* (2006.01)

(52) U.S. Cl.
CPC .............. *A61M 5/31515* (2013.01); *A61M 2005/31516* (2013.01); *A61M 2207/00* (2013.01); *A61M 2207/10* (2013.01)

(58) Field of Classification Search
USPC ........................................................ 604/506
See application file for complete search history.

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 8,585,658 B2 | 11/2013 | Forstreuter | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2008/0234633 A1* | 9/2008 | Nielsen ............... | A61M 5/24 604/208 |
| 2009/0275916 A1 | 11/2009 | Harms et al. | |

FOREIGN PATENT DOCUMENTS

| | | |
|---|---|---|
| EP | 0937476 A2 | 8/1999 |
| WO | 9938554 A1 | 8/1999 |
| WO | 0110484 A1 | 2/2001 |
| WO | 2007017051 A1 | 2/2007 |
| WO | 2010124961 A1 | 11/2010 |
| WO | 2011032229 A1 | 3/2011 |
| WO | 2012017035 A1 | 2/2012 |

* cited by examiner

DRUG DELIVERY DEVICE AND METHOD FOR ELIMINATING A CLEARANCE OF THE PISTON ROD FOR DRUG DELIVERY DEVICES

CROSS REFERENCE TO RELATED APPLICATIONS

The present application is a U.S. National Phase Application pursuant to 35 U.S.C. § 371 of International Application No. PCT/EP2014/054530 filed Mar. 10, 2014, which claims priority to European Patent Application No. 13159053.1 filed Mar. 13, 2013. The entire disclosure contents of these applications are herewith incorporated by reference into the present application.

FIELD OF INVENTION

Drug delivery devices, in particular pen-type injection devices, comprise a bung for the ejection of a dose of a drug and a piston rod driving the bung. The piston rod may be provided with a mechanism for setting and delivering a dose. At the end of the assembly of the device a gap may intentionally be left between the end of the piston rod, which may be provided with a bearing, and the bung, which may be provided as part of a drug cartridge. The gap is a consequence of the tolerances associated with all the assembled parts and the desire not to preload the bung in the assembled device before the first usage takes place.

BACKGROUND

When the device is used for the first time, the dose of a drug actually delivered will be less than the dose set, and the difference will equal the volume that would be ejected if the bung were travelling at the speed of the piston rod before the piston rod gets into contact with the bung. For many drugs this loss is significant and can cause the first dose to be well outside the allowable dose accuracy limits. The user is therefore instructed to perform a priming step like 'air shot' prime doses until fluid begins to be ejected.

SUMMARY

It is an object of the present invention to provide a way of avoiding a priming step for drug delivery devices comprising a piston rod that is provided to drive a bung.

This object is achieved with the drug delivery device according to claim 1 and with the method for eliminating a clearance of the piston rod for drug delivery devices according to claim 13. Embodiments and variants derive from the dependent claims.

A piston rod according to this invention shall mean any member that is intended to drive a piston or bung of a drug delivery device and may particularly be a lead screw.

The drug delivery device comprises a piston rod arrangement in an assembled state before the first use, comprising a piston rod, a bung, which is intended to be driven by the piston rod, a body member, and a drive member provided to advance the piston rod. The piston rod is threadedly engaged with the body member, and the drive member is threadedly engaged with the piston rod and movable relative to the body member. A mechanism is provided that defines unit steps of movement of the drive member and corresponding unit steps of movement of the piston rod. The piston rod is arranged in contact with the bung or at a distance from the bung that is less than a distance of one corresponding unit step of movement. The body member may be a housing or an inner body, which is arranged in an outer body.

The piston rod arrangement is assembled so that the drug delivery device is ready for use, but no dose of a drug has yet been expelled. This state is obtained at the end of the manufacture and before the first dose of a drug has been selected by a user. The provided amount of drug is therefore not reduced by an air shot or a similar priming step.

In an embodiment of the drug delivery device, the piston rod is arranged at a distance from the bung that is less than a distance of half a corresponding unit step of movement. In this embodiment a greater accuracy is achieved.

In a further embodiment of the drug delivery device, the mechanism defining unit steps of movement is formed by a feature acting between the body member and the drive member.

In a further embodiment of the drug delivery device, a dial member is coupled with the drive member, and the mechanism defining unit steps of movement is provided by a feature formed on the body member and on the dial member. The dial member may also be used to indicate an amount of a drug, for example.

In a further embodiment of the drug delivery device, the drive member comprises a first part and a second part, coupled in such a manner that the first part and the second part can rotate relative to one another. The second part is threadedly engaged with the piston rod. A rotation of the piston rod does not involve a rotation of the first part.

A further embodiment of the drug delivery device further comprises a button member comprising an operation button, the first part of the drive member being arranged between the second part and the button member. A first locking feature of the button member is engaged with a corresponding feature of the first part of the drive member, the first locking feature rotationally locking the button member with the first part.

A further embodiment of the drug delivery device further comprises a second locking feature of the button member, the second locking feature being engaged with a corresponding feature of the second part of the drive member, the second locking feature rotationally locking the button member with the second part.

In a further embodiment of the drug delivery device, the drive member comprises a first part and a second part, which is threadedly engaged with the piston rod. A coupler is fastened to the second part, and the first part and the second part are releasably rotationally locked by the coupler. The coupler forms a clutch, so that a rotation of the piston rod can be accompanied with a rotation of the first part or not.

In a further embodiment of the drug delivery device, a ramp feature is provided on the body member. A further body member, which may be an outer body, for example, is provided with a corresponding ramp feature. The ramp features are provided to transform a relative rotation of the body member and the further body member into a relative shift. Thus the clutch can be engaged and disengaged by a relative rotation of the body members.

A further embodiment of the drug delivery device further comprises threads threadedly engaging the piston rod with the body member and further threads threadedly engaging the piston rod with the drive member. The thread of the body member has an area of contact on the body member, and the thread of the drive member has an area of contact on the drive member. The areas of contact are in contact with the piston rod in such a manner that no backlash between the drive member, the piston rod and the body member interferes with an advancement of the piston rod by the drive member or that a backlash between the drive member, the piston rod and the body member is so small that the backlash only causes a reduction of the advancement of the piston rod by less than a distance of one corresponding unit step of movement.

In a further embodiment the drug delivery device is a disposable device, which is not refilled when it is empty, and/or a variable dose device, which can be used to dispense different selected amounts of a drug. The drug delivery device may especially be an injection device, in particular a pen-type injector.

In a further aspect the invention relates to a method for eliminating a clearance of a piston rod for drug delivery devices, comprising the steps of assembling a piston rod, a bung, and a drive member provided for generating a movement of the piston rod in a body member in such a manner that the piston rod is arranged at a distance from the bung, the bung is stationary with respect to the body member, and the piston rod is threadedly engaged with the body member and with the drive member. The piston rod is advanced with respect to the body member towards the bung, until the piston rod is stopped by the bung. The drive member is rotated until the piston rod begins to advance again, the drive member is then stopped, and the piston rod is fixed at or near the position obtained.

In a variant of the method the drive member is rotated in increments of unit steps of movement generating a corresponding advancement of the piston rod as long as the piston rod is free to advance, and the drive member is stopped at the end of a unit step of movement that is not accompanied by a corresponding advancement of the piston rod.

In a further variant of the method a backlash between the piston rod, the drive member and the body member is determined beforehand. The drive member is rotated in increments of unit steps of movement generating a corresponding advancement of the piston rod as long as the piston rod is free to advance. When a unit step of movement is not accompanied by a corresponding advancement of the piston rod, the drive member is further rotated until the backlash is removed.

In a further variant of the method the drive member is rotated in increments of unit steps of movement generating a corresponding advancement of the piston rod as long as the piston rod is free to advance. After an increment that is not accompanied by a corresponding advancement of the piston rod, the drive member is further rotated until the end of a first increment that is again accompanied by a corresponding advancement of the piston rod is reached. The drive member is then rotated back by one unit step or by two unit steps, depending on the preceding advancement of the piston rod.

In a further variant of the method the advancement of the piston rod is determined by a measurement of a torque reacting on the drive member.

The method for eliminating a clearance of a piston rod for drug delivery devices can instead comprise the steps of assembling a piston rod, a bung and a drive member in a body member in such a manner that the bung is stationary with respect to the body member, and the piston rod is threadedly engaged with the body member and with the drive member. A frictional force is used to generate a torque acting between the body member and the drive member. The body member is shifted in the direction towards the bung, driving the piston rod into contact with the bung and generating a rotation of the piston rod, which causes a rotation of the drive member against the action of the torque. The piston rod is driven into contact with the bung against the action of said torque by a force loading the bung with a resilient force.

The term "drug", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
  H-(Lys)4-des Pro36, des Pro37 Exendin-4(1-39)-NH2,
  H-(Lys)5-des Pro36, des Pro37 Exendin-4(1-39)-NH2,
  des Pro36 Exendin-4(1-39),
  des Pro36 [Asp28] Exendin-4(1-39),
  des Pro36 [IsoAsp28] Exendin-4(1-39),
  des Pro36 [Met(O)14, Asp28] Exendin-4(1-39),
  des Pro36 [Met(O)14, IsoAsp28] Exendin-4(1-39),
  des Pro36 [Trp(O2)25, Asp28] Exendin-4(1-39),
  des Pro36 [Trp(O2)25, IsoAsp28] Exendin-4(1-39),
  des Pro36 [Met(O)14 Trp(O2)25, Asp28] Exendin-4(1-39), des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Trp(O2)25] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-H2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa http://en.wikipedia.org/wiki/Dalton_%28unit%29) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

The following is a detailed description of embodiments of the mechanism and drug delivery device in conjunction with the appended drawings.

DETAILED DESCRIPTION

Figure 1:
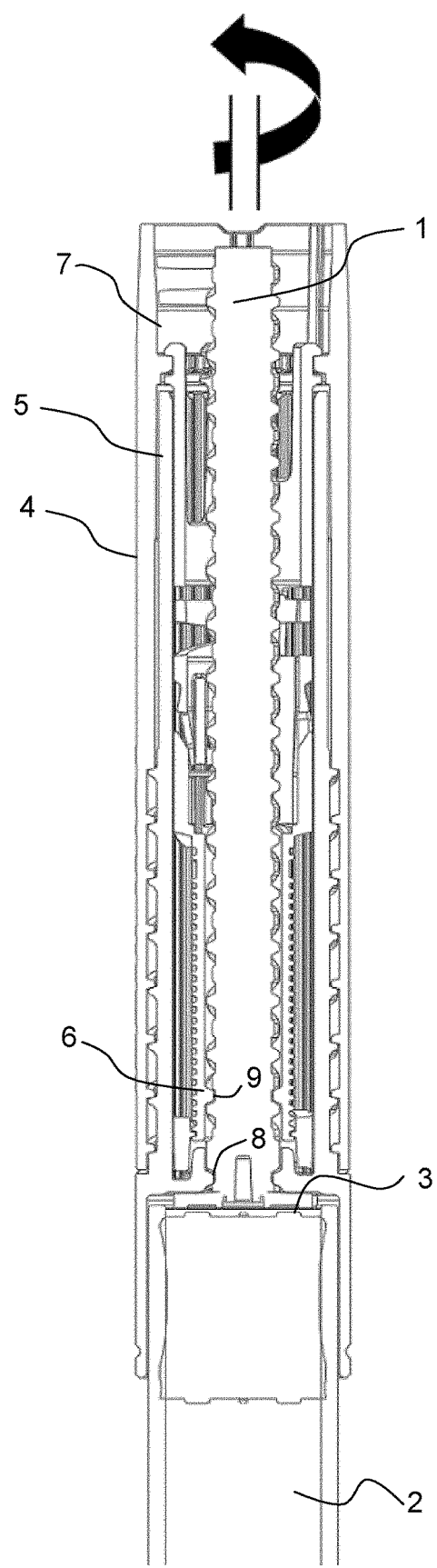
FIG. 1 is a cross section of a pen-type drug delivery device showing a piston rod.
Figure 1A:
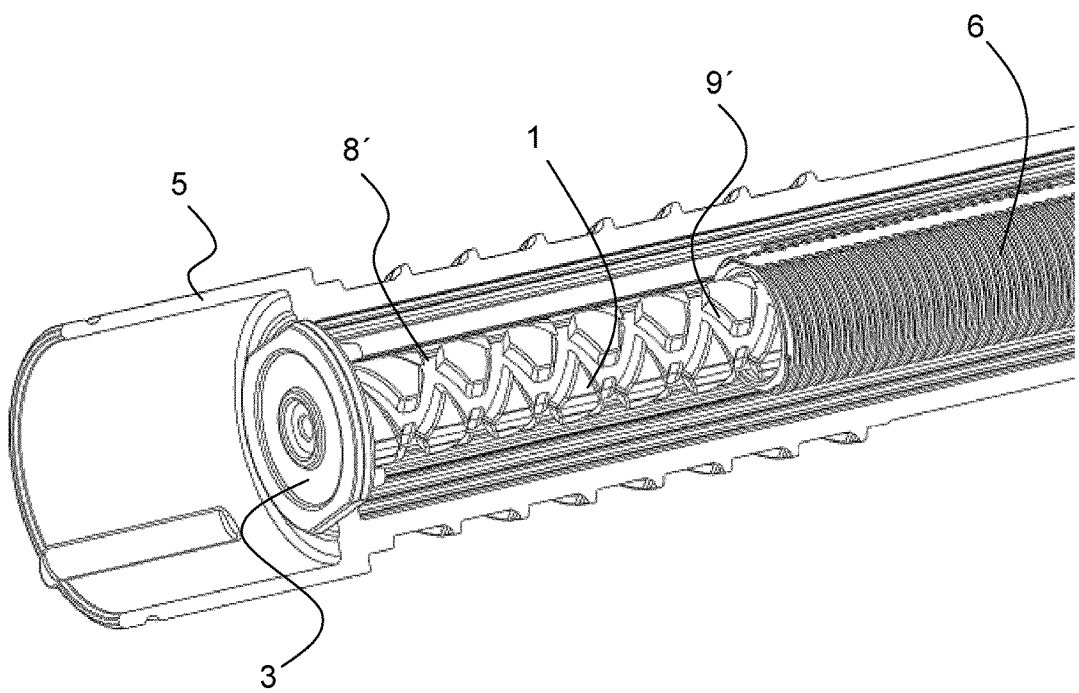
FIG. 1a is a perspective view of a detail of FIG. 1.

FIG. 1 shows a cross section of an example of a drug delivery device including a piston rod arrangement. FIG. 1a shows a detail thereof in a perspective view. The piston rod 1 is provided to advance a bung 2, which serves to eject a dose of a drug and may be provided in a drug receptacle like a cartridge. A bearing 3 may be provided between the piston rod 1 and the bung 2 to facilitate a relative movement between the piston rod 1 and the bung 2, in particular a relative rotation. The piston rod arrangement is located inside a housing, which comprises at least a body member 5, which may be an inner body 5 arranged in an outer body 4, for example. A drive member 6 is provided to advance the piston rod 1, which is threadedly engaged with the inner body 5 and with the drive member 6. A threaded engagement between the piston rod 1 and the inner body 5 may be formed by a thread 8 on the inner body 5 and a thread 8' on the piston rod 1, and a threaded engagement between the piston rod 1 and the drive member 6 may be formed by a thread 9 on the drive member 6 and a further thread 9' on the piston rod 1. The threads 8', 9' of the piston rod 1 may have opposite senses of rotation and may be arranged intersecting one another, as shown in FIG. 1a. A dial member 7, which may also be used to indicate an amount of a dose, for example, may be arranged between the outer body 4 and the inner body 5 and may be coupled with the drive member 6. This mechanism will now be described in more detail as a typical example of a mechanism comprising a piston rod arrangement, but the invention can be applied in conjunction with other mechanisms as well.

The mechanism is used to select a dose of a drug that is to be delivered. A rotation of the drive member 6 with respect to the outer body 4 and the inner body 5 is effected by a suitable operation means like a user button. During dialing the drive member 6 and the dial member 7 are rotationally locked, so that they are simultaneously rotated, and are axially coupled, so that they do not shift relative to one another in the direction of the longitudinal extension of the piston rod 1. During the rotation of the drive member 6, the piston rod 1 is held fixed with respect to the inner body 5. The threaded engagement between the piston rod 1 and the drive member 6 causes the drive member 6 to advance along the piston rod 1 in the direction away from the bung 2 during dialing.

After dialing the dose set can be delivered by pushing the drive member 6 in the direction towards the bung without rotating the drive member 6 relative to the outer body 4 and the inner body 5. The interaction of the threaded engagements between the piston rod 1, the inner body 5 and the drive member 6 causes an advancement of the piston rod 1 according to the pitches. During dose delivery the inner body 5 and the drive member 6 are rotationally locked, so that they do not rotate relative to one another, and the drive member 6 and the dial member 7 are axially locked, so that they advance simultaneously in the direction towards the bung, and the helically advancing dial member 7 may be used to indicate the amount of the drug already delivered.

The mechanism can be assembled with all components in place except for the operation button. In this state the drive member 6 is neither rotationally fixed to the dial member 7 nor to the inner body 5. Therefore, an axially static rotation of the drive member 6, indicated by the curved arrow in FIG. 1, causes a helical advancement of the piston rod 1 with respect to the inner body 5 because of the threaded engagements of the piston rod 1 with the inner body 5 and the drive member 6. The straight arrow indicates a predefined force that is applied to the piston rod 1. This force could be applied using a spring, weights, pneumatics, electromechanical devices or the like and presets a compression of the bung 2. When the piston rod 1 backs off, the remaining clearance between the bearing 3 and the bung 2 is equal to the back-off distance minus the distance due to the bung compression. A compression of the bung 2 may thus be used to adjust the volume of the first dose delivered from an unused cartridge. The axial position of the piston rod 1 may be measured using an LVDT (linear variable differential transformer) or another suitable displacement sensor, for instance. To advance the piston rod 1 towards the bung 2 the drive member 6 is rotated. By measuring the position of the piston rod 1 as it advances it is possible to determine when the piston rod 1 contacts the bung 2. After the adjustment is completed the operation button can be assembled to the device.

Figure 2:
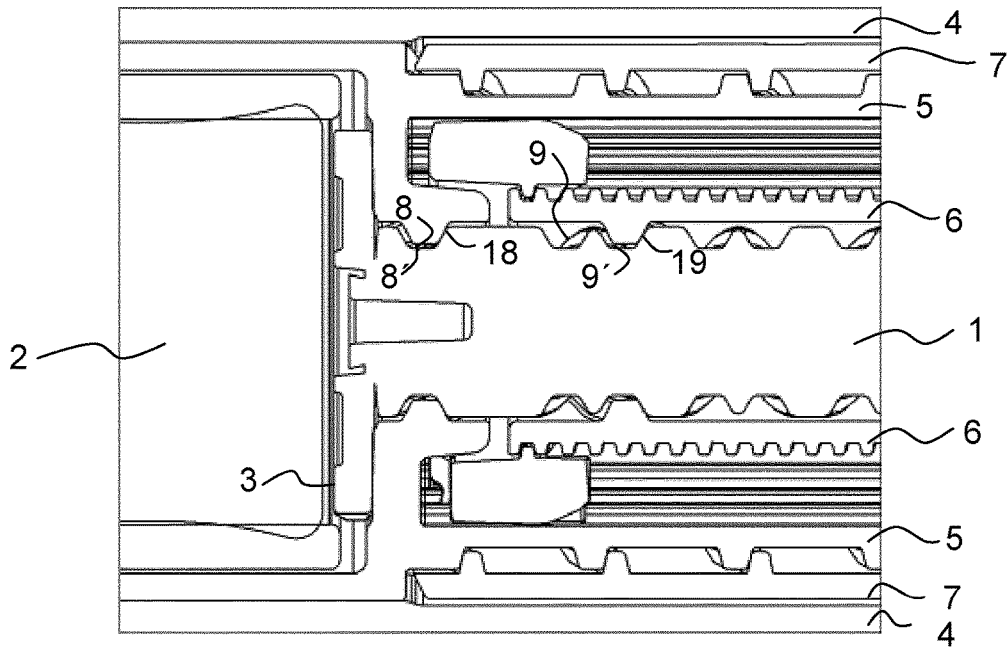
FIG. 2 is a cross section of an arrangement of a piston rod and a bung at a starting position.

FIGS. 2 to 7 show a section of the cross section according to FIG. 1 for different states of operation of an arrangement of a piston rod 1 and a bung 2 within the mechanism. FIG. 2 shows a starting position. There is some axial clearance or backlash in the threaded engagements. The axial force applied to the piston rod 1 pushes the piston rod 1 towards the bung 2 until the clearances of the threaded engagements are removed in this direction and corresponding features of the threaded engagements are in contact. If the threaded engagements are effected by threads 8, 8' coupling the piston rod 1 and the inner body 5 and threads 9, 9' coupling the piston rod 1 and the drive member 6, for example, there is some axial clearance or backlash between the interfaces of the threads 8, 8', 9, 9'. When interfaces of one of the threads 8, 8', 9, 9' have come into contact, the piston rod 1 slides helically along this thread until interfaces of the other thread come into contact, too, and the clearance or backlash is completely removed in this direction. If one of the threads 8', 9' of the piston rod 1 is right-handed and the other one is left-handed, as may be the case in preferred embodiments of the mechanism, the area of contact 18 of the thread 8 of the inner body 5 and the area of contact 19 of the thread 9 of the drive member 6 are both located on the side facing away from the bung 2. If the threads 8', 9' have the same sense of rotation but different pitches, the areas of contact on the thread interfaces of the inner body 5 and the drive member 6 are located on opposite sides, one facing towards and one facing away from the bung 2, but the basic idea of the following description is the same in both cases.

When the threaded engagement between the piston rod 1 and the drive member 6 is in contact, a rotation of the drive member 6 allows the piston rod 1 to advance according to the threaded engagement with the inner body 5, the piston rod 1 being driven by the preload force. The areas of contact 18, 19 of the thread interfaces on the inner body 5 and on the drive member 6 remain on their initial side, which is typically the side facing away from the bung 2. When the axial movement of the piston rod 1 is stopped by the bung 2, and the drive member 6 is further rotated, the threaded engagement between the piston rod 1 and the drive member 6 is temporarily removed because of the clearance or backlash in the threaded engagement between the piston rod 1 and the drive member 6. When interfaces of the threaded engagement between the piston rod 1 and the drive member 6 are again in contact, the area of contact 19 of the thread 9 of the drive member 6 is on the side facing towards the bung 2. When the drive member 6 is now further rotated, the drive member 6 rotates the piston rod 1 in such a manner that the threaded engagement between the piston rod 1 and the inner body 5 is temporarily removed because of the clearance or backlash in the threaded engagement between the piston rod 1 and the inner body 5. When the threads 8, 8' are again in contact, the area of contact 18 of the thread 8 of the inner body 5 is also on the side facing towards the bung 2. The areas of contact 18, 19 of the thread interfaces of the inner body 5 and the drive member 6 are now both located on the side that is opposite the side where the areas of contact were previously located. This change of condition will be referred to as "taking up the backlash" in the following description. The compressed bung 2 exerts an axial force on the piston rod 1, which compensates for the preload force and keeps the threaded engagements in contact.

Figure 3:
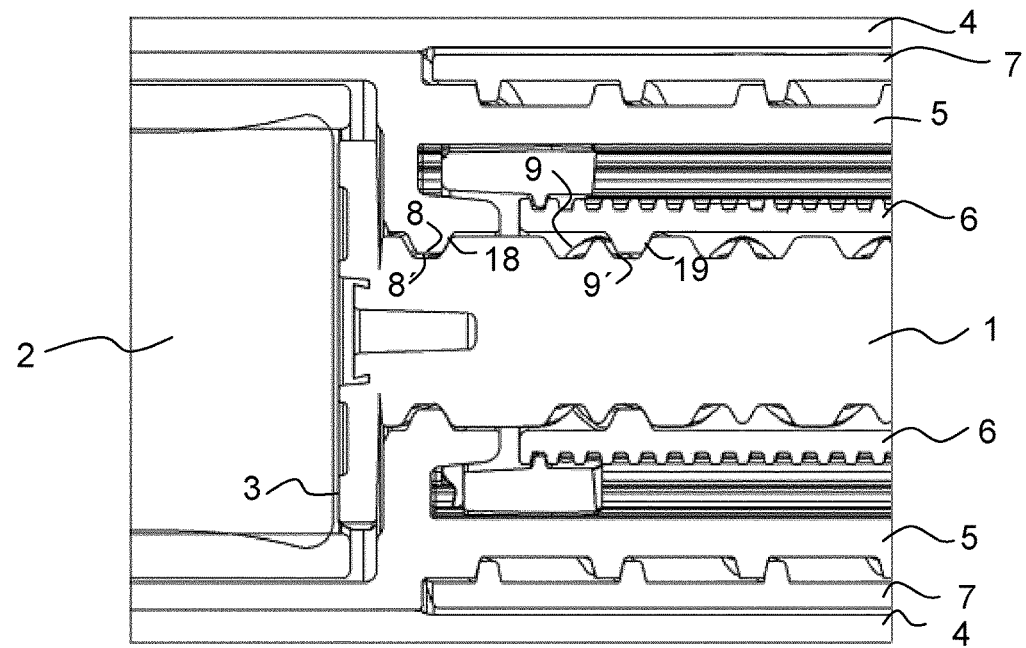
FIG. 3 is a cross section according to FIG. 2 for a later state of operation.

FIG. 3 shows the piston rod arrangement according to FIG. 2 after a rotation of the drive member 6 corresponding to one unit of dialing, but without an axial displacement of the drive member 6 that would occur in the totally assembled device. The piston rod 1 has advanced correspondingly. The threads 8, 8', 9, 9' are still in contact, the areas of contact 18, 19 on the inner body 5 and on the drive member 6 being located on sides facing away from the bung 2.

Figure 4:
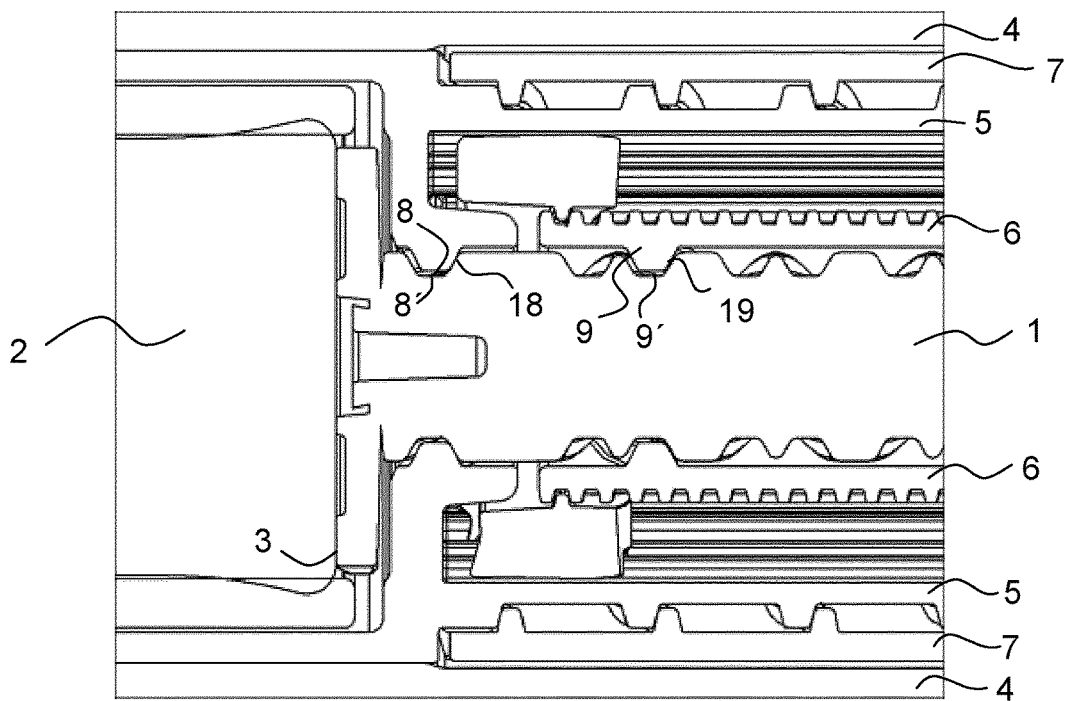
FIG. 4 is a cross section according to FIG. 3 for still a later state of operation.

FIG. 4 shows the piston rod arrangement according to FIG. 3 for a state in which the drive member 6 has further been rotated by one unit, and the piston rod 1 has intermediately stopped advancing when the reaction force from the bung 2 is equal to the preload force. The areas of contact 18, 19 on the inner body 5 and on the drive member 6 being still located on sides facing away from the bung 2.

Figure 5:
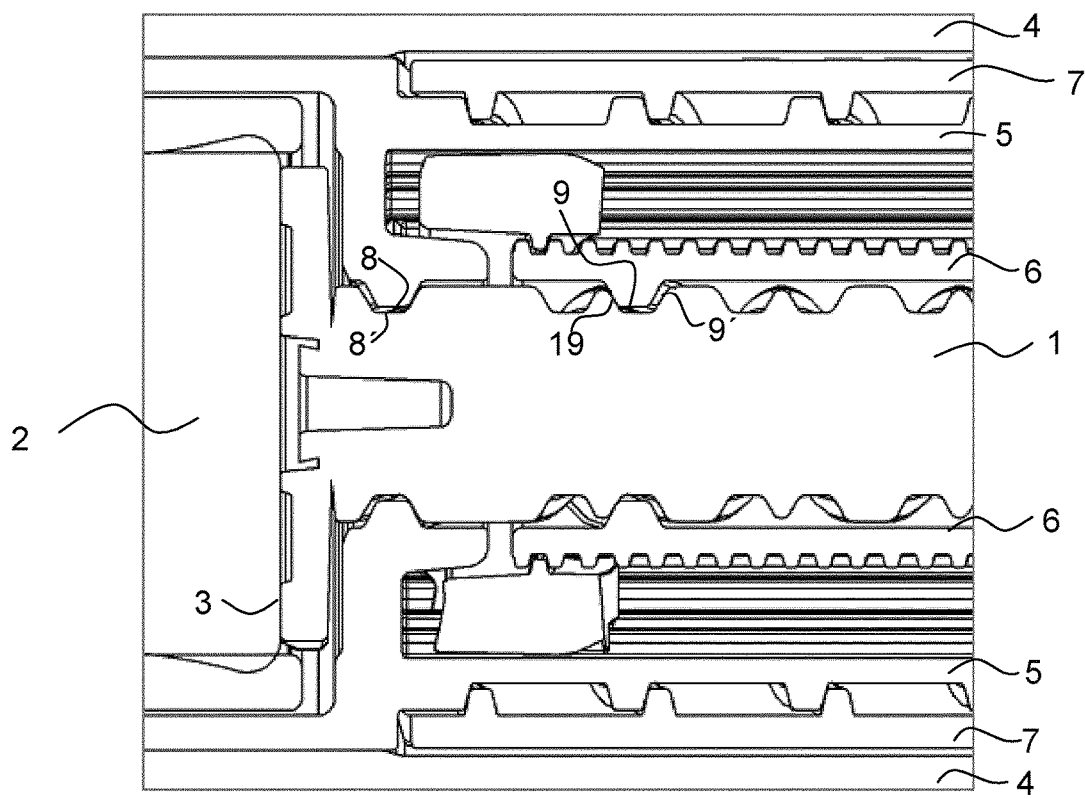
FIG. 5 is a cross section according to FIG. 4 for an intermediate position.

FIG. 5 shows the piston rod arrangement according to FIG. 4 with the components shown in an intermediate position, after the drive member 6 has further been rotated by half a unit. The backlash in the thread interface between the piston rod 1 and the drive member 6 has now been taken up, so that the area of contact 19 on the drive member 6 is on the side facing towards the bung 2. The piston rod 1 is caused to rotate by the rotation of the drive member 6, thus temporarily removing the thread contact with the inner body 5, so that the piston rod 1 does not advance axially.

Figure 6:
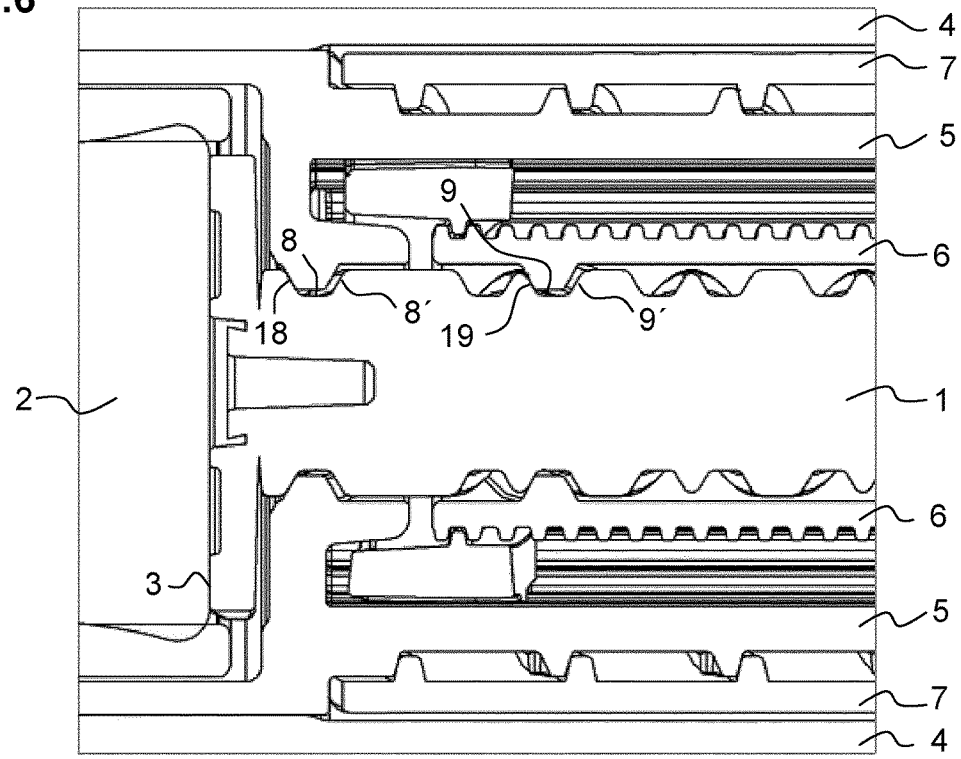
FIG. 6 is a cross section according to FIG. 5 for a later state of operation.

FIG. 6 shows the piston rod arrangement according to FIG. 5 for a further state in which the backlash in both threaded engagements has been taken up. Interfaces of both threads 8, 8', 9, 9' are again in contact, and the areas of contact 18, 19 on the inner body 5 and on the drive member 6 are now located on sides facing towards the bung 2. The piston rod 1 is now able to advance in the direction towards the bung 2 if the drive member 6 is further rotated.

Figure 7:
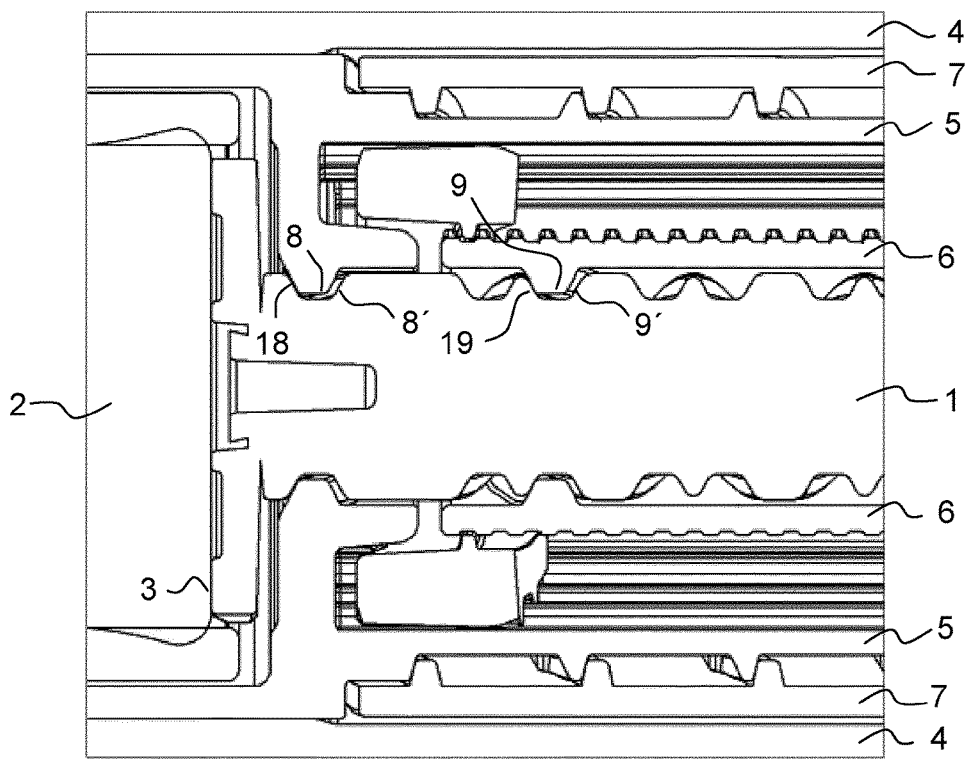
FIG. 7 is a cross section according to FIG. 6 for still a later state of operation.

FIG. 7 shows the piston rod arrangement according to FIG. 6 for the state in which the piston rod 1 again advances by increments of one unit as the drive member 6 is rotated according to units dialed.

Figure 8:
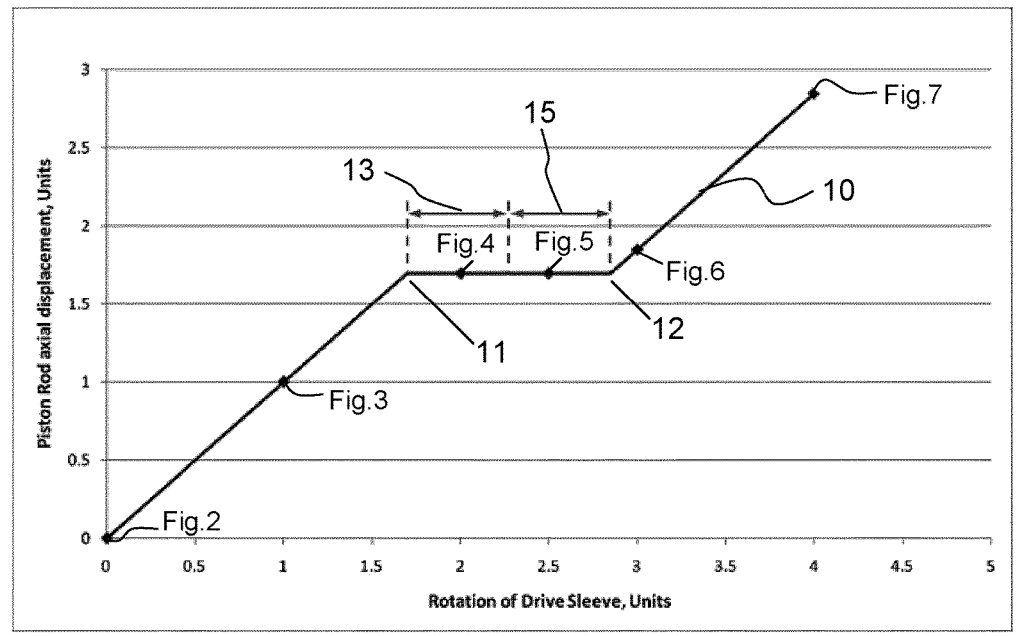
FIG. 8 is a diagram showing the piston rod position vs. drive member rotation.

FIG. 8 shows a diagram representing the axial position or displacement of the piston rod 1, indicated in units of increments on the ordinate, as a function of the rotation of the drive member 6, indicated in units of rotation on the abscissa. Marked points on the graph 10 correspond to the sequence of operation according to FIGS. 2 to 7. There is a horizontal portion of the graph 10 corresponding to the state of operation in which the drive member 6 rotates but the piston rod 1 does not advance. The horizontal portion of the graph 10 begins at the point 11 when the reaction force from the bung 2 is equal to the preload force applied to the piston rod 1 and ends at the target stop point 12 when the backlash has been taken up and the piston rod 1 again begins to advance. In a first phase 13 in which the piston rod 1 remains stationary the backlash between the drive member 6 and the piston rod 1 is taken up, according to FIG. 4. In a second phase 14 in which the piston rod 1 remains stationary the backlash between the piston rod 1 and the inner body 5 is taken up, according to FIG. 5. It is desirable for the assembly process to finish with the device in the condition where the backlash has just been taken up and the piston rod 1 is ready to move forwards in the direction towards the bung 2. In embodiments in which the drive member 6 must rest in one of a number of discrete positions defined by the inner body 5, the highest accuracy that can be achieved is ±0.5 units. The accuracy may be higher for other types of mechanism.

Figure 9:
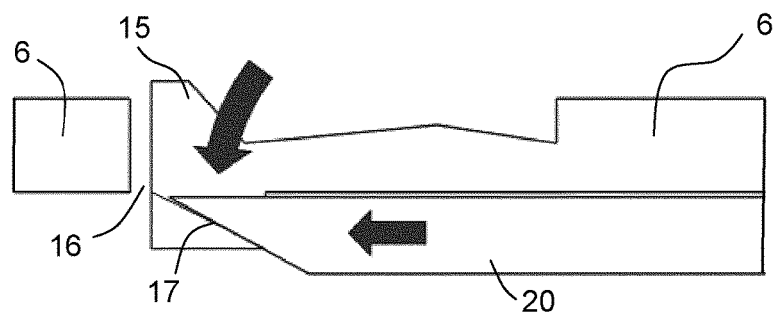
FIG. 9 is a schematic cross section of a clicker mechanism that is disengaged during assembly.

If a feature like a clicker arm is provided on the drive member 6 to restrict the advancement of the piston rod 1 to increments of one unit, this feature may be disengaged during assembly by a suitable assembly tool, which may be adapted, for example, to deflect the feature out of engagement. FIG. 9 is a schematic cross section of a clicker mechanism that is disengaged during assembly. The drive member 6 is provided with at least one flexible clicker arm 15, which extends into a gap 16 of the drive member 6 and exceeds an outer diameter of the drive member 6. The clicker arm 15 is intended to engage with corresponding features on an inner surface of the inner body 5, which may be splines, for example, to define discrete rotational positions for the drive member 6 and the dial member 7 and to inhibit a rotation of the drive member 6 during dose delivery. During assembly the clicker arm 15 is deflected in the direction of the curved arrow shown in FIG. 9 by an interaction of a tilted surface 17 of the drive member 6 with a tapered assembly tool 20, which is moved in the direction of the straight arrow shown in FIG. 9. Thus the clicker arm 15 is disengaged from the inner body 5, and the drive member 5 and the piston rod 1 are free to rotate and advance continuously.

Figure 10:
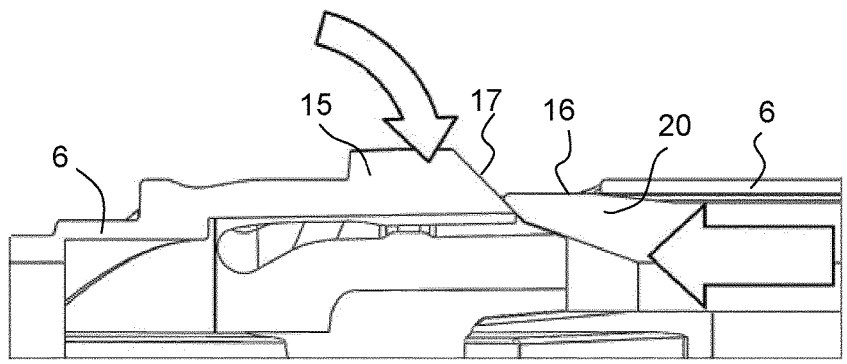
FIG. 10 is a schematic cross section according to FIG. 9 for a further embodiment.

FIG. 10 shows a further embodiment, in which the tilted surface 17 of the drive member 6 is located at the clicker arm 15 at a position that is different from the corresponding position in the embodiment according to FIG. 9. The shape of the assembly tool 20 is adapted to the design of the clicker arm 15 and the position of the tilted surface 17. During assembly the clicker arm 15 is deflected in the direction of the curved arrow shown in FIG. 10 by an interaction of the tilted surface 17 of the drive member 6 with the tapered assembly tool 20, which is moved in the direction of the straight arrow shown in FIG. 10.

There are various methods by which the positions of the piston rod 1 that are detected during the assembly can be interpreted to determine the optimal initial position of the piston rod 1. FIGS. 11 to 17 are diagrams showing the piston rod position vs. drive member rotation for different modes of operation.

Figure 11:
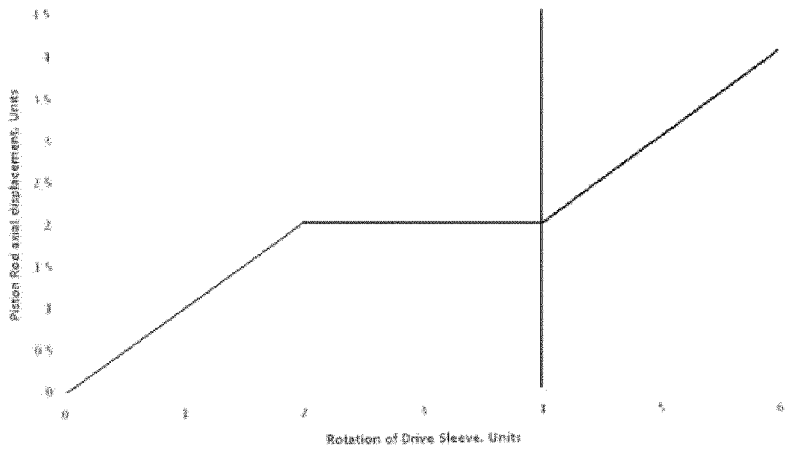
FIG. 11 is a diagram showing the piston rod position vs. drive member rotation for continuous motion bung detect.

FIG. 11 is a diagram showing the piston rod position vs. drive member rotation if the piston rod 1 is advanced in a continuous motion, rather than in increments of unit steps of movement. The movement or the position of the piston rod 1 is constantly monitored, so that the period when it is not moving axially can be detected. This period is represented by the horizontal portion of the graph in the diagram of FIG. 11. As soon as the piston rod begins to advance again, indicated in the diagram of FIG. 11 by the vertical line, it is in its optimal initial condition where it is preferably fixed. If an assembly tool 18 as shown in FIGS. 9 and 10 is used, it is removed so that the clicker arm 15 is released to occupy the nearest position corresponding to a unit step of movement.

Figure 12:
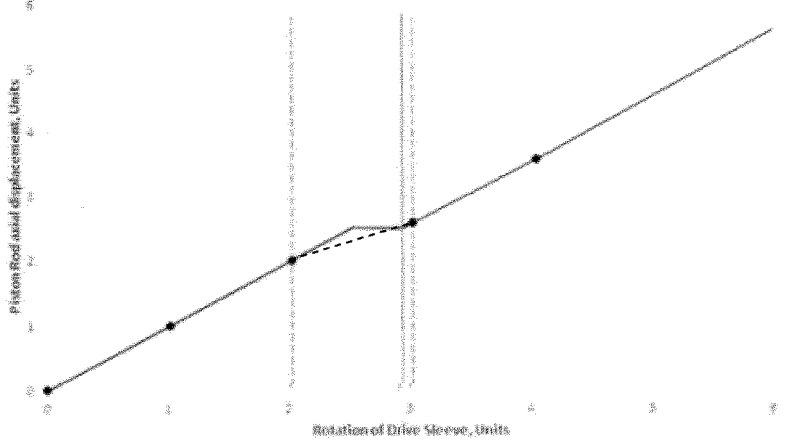
FIG. 12 is a diagram showing the piston rod position vs. drive member rotation for bung detect less than 0.5 units backlash.

FIG. 12 is a diagram showing the piston rod position vs. drive member rotation for the case in which the piston rod 1 is advanced in increments of unit steps of movement and there is a backlash corresponding to less than half a unit step of movement in the thread interfaces. In this case the accuracy is reduced below the range of ±0.5 unit steps that is otherwise achievable. The rotation of the drive member 6 is stopped at the first increment of one unit step of movement with less than one unit step of axial travel of the piston rod 1, indicated in the diagram of FIG. 12 by the interval between the broken vertical lines. The piston rod 1 starts moving again at some point within the one-unit step, indicated in the diagram of FIG. 12 by the solid vertical line, and this point cannot be determined beforehand for all copies of the mechanism. The accuracy is therefore reduced to one unit minus the backlash distance.

Figure 13:
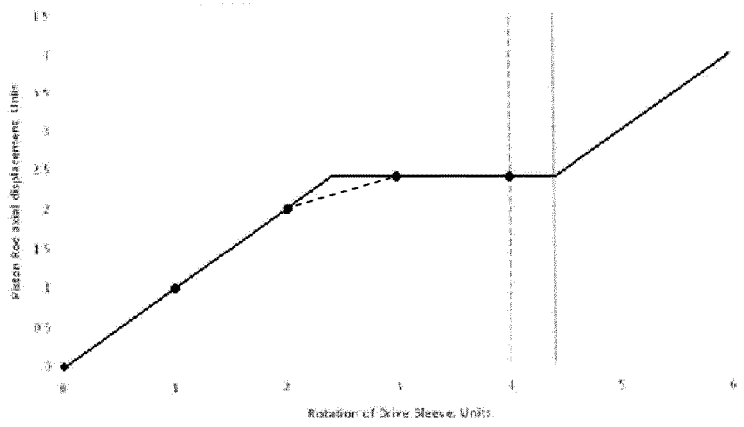
FIG. 13 is a diagram showing the piston rod position vs. drive member rotation for bung detect with known backlash.

FIG. 13 is a diagram showing the piston rod position vs. drive member rotation for the case in which the amount of backlash is known to be larger than one unit step of movement and is considered to be consistent between each set of parts. The drive member 6 is rotated in increments of unit steps of movement, generating corresponding advancements of the piston rod 1, until there is a first unit step of movement for which the advancement of the piston rod 1 is found to be less than the advancement corresponding to one unit step. The drive member 6 is then further rotated to advance the piston rod 1 by the known backlash distance minus the shortfall in the immediately preceding increment. The rotation of the drive member 6 to the last unit step before the piston rod 1 starts moving again is indicated by the broken vertical line in the diagram of FIG. 13, and the piston rod 1 starts moving again within the next unit step, indicated by the solid vertical line in the diagram of FIG. 13. When this method is applied the drive member 6 need not be rotated in the reverse direction.

Figure 14:
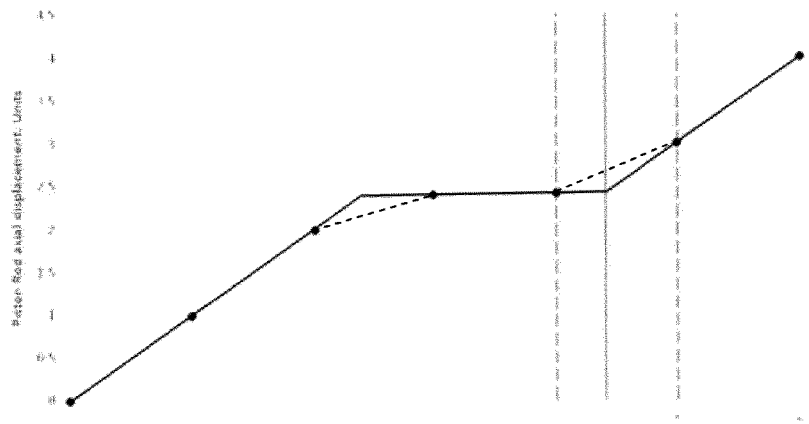
FIG. 14 is a diagram showing the piston rod position vs. drive member rotation for over travel bung detect.

FIG. 14 is a diagram showing the piston rod position vs. drive member rotation for the case of a backlash distance corresponding to more than half a unit step of movement if the amount of backlash in the device is not precisely known. When a rotation of the drive member 6 corresponding to an increment of one unit step does not advance the piston rod 1 by a corresponding unit of axial travel, contact has been made with the bung 2. When a further increment by one unit step of movement is found to be accompanied by a corresponding one-unit step of advancement of the piston rod 1, the rotation of the drive member 6 is stopped. This condition indicates that the movement of the piston rod 1 has already started again at the point indicated in the diagram of FIG. 14 by the solid vertical line between the broken vertical lines limiting the preceding increment of one unit step. A decision may be taken whether to rewind the drive member 6 by one or two units, depending on the displacement measured during the preceding increment, which is the one between the broken vertical lines in the diagram of FIG. 14. If the travel of the piston rod 1 measured corresponded to less than 0.5 unit steps, the drive member 6 is preferably rotated back by one unit, and if the travel of the piston rod 1 measured corresponded to more than 0.5 unit steps, the drive member 6 is preferably rotated back by two units.

Figure 15:
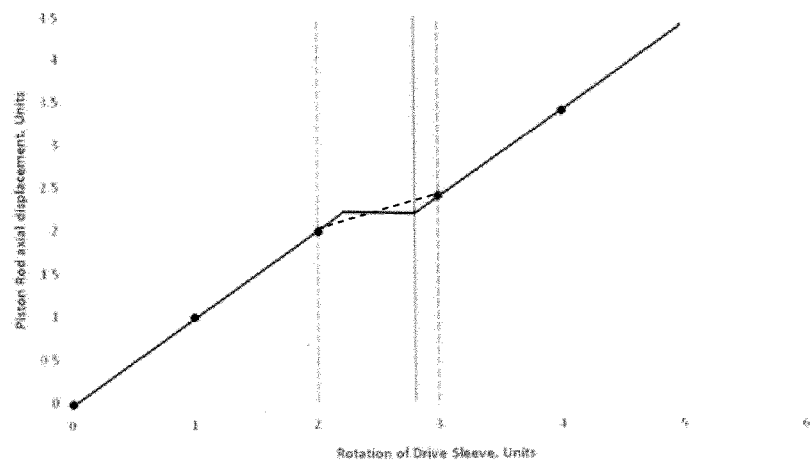
FIG. 15 is a diagram showing the piston rod position vs. drive member rotation for one increment after short increment bung detect.

FIG. 15 is a diagram showing the piston rod position vs. drive member rotation for the case of a backlash distance that is known to correspond to 0.5 to 1 unit steps of movement, if the amount of the backlash is not precisely known. In this case there will be one or two increments in the rotation of the drive member 6 generating an axial travel of the piston rod corresponding to less than one unit step, as shown in the diagram of FIG. 15 in the range between the broken vertical lines for the case of one such increment. When an increment with less than one unit of axial travel of the piston rod 1 is measured, the drive member 6 will be rotated by one further increment and then stopped. The total amount of backlash can now be determined and the piston rod 1 can be positioned accordingly.

Figure 16:
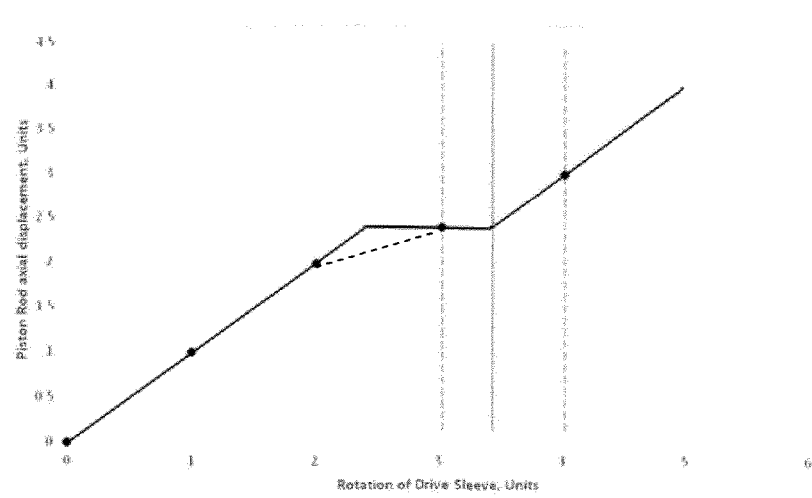
FIG. 16 is a diagram showing the piston rod position vs. drive member rotation for stop at second short increment bung detect.

FIG. 16 is a diagram showing the piston rod position vs. drive member rotation for the case of a backlash distance that is known to correspond to 1 to 2 unit steps of movement, if the amount of the backlash is not precisely known. In this case there will be at least two increments with less than one unit of travel of the piston rod 1, but there may or may not be an increment that does not generate an advancement of the piston rod 1 at all. When the second increment with less than one unit of travel of the piston rod 1 is measured, the rotation of the drive member 6 is stopped. If the travel of the piston rod 1 measured corresponds to less than 0.5 unit steps, the piston rod 1 and the drive member 6 are left in position. If the travel of the piston rod 1 measured corresponds to more than 0.5 unit steps, the drive member 6 is preferably rotated back by one unit step.

Figure 17:
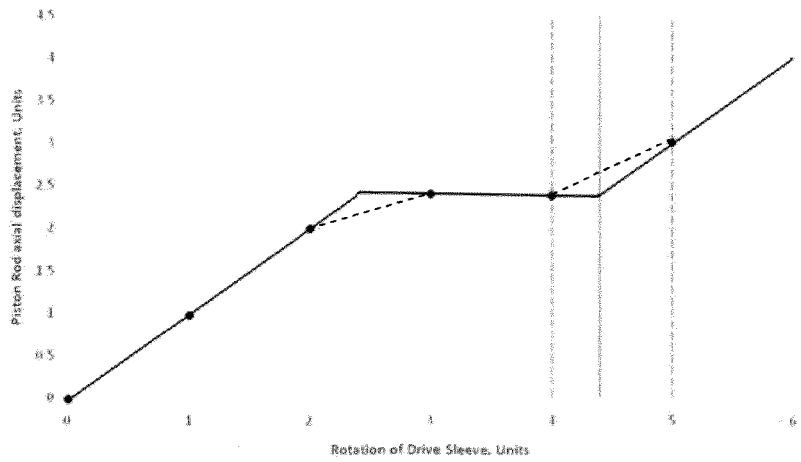
FIG. 17 is a diagram showing the piston rod position vs. drive member rotation for stop after flat bung detect.

FIG. 17 is a diagram showing the piston rod position vs. drive member rotation for the case of any backlash distance over two units, if the amount of the backlash is not precisely known. In this case there will be at least one increment with no axial travel of the piston rod 1. When an increment results in a further advancement of the piston rod 1, the rotation of the drive member 6 is stopped. If the travel of the piston rod 1 measured corresponds to less than 0.5 unit steps, the piston rod 1 and the drive member 6 are left in position. If the travel of the piston rod 1 measured corresponds to more than 0.5 unit steps, the drive member 6 is preferably rotated back by one unit step.

If the drive member 6 can be rotated continuously, it is possible to measure the reaction torque as the drive member 6 is rotated. Features generating discrete rotation steps like clicker arms can be disengaged as described in conjunction with FIGS. 9 and 10 in order to allow a continuous rotation of the drive member 6. If the reaction torque is measured a direct detection of the axial position of the piston rod 1 is not required. The drive member 6 is rotated until a predefined torque, corresponding to a certain force acting on the bung 2, is reached. This torque can be measured using a torque cell or a slip clutch, for example, or by means of any other appropriate measuring device, which is known per se. When the predefined torque is reached, the drive sleeve 6 is rotationally locked, which may be achieved by releasing the clicker arms, for example. The assembly can then be finished, in particular by mounting the operation button.

Figure 18:
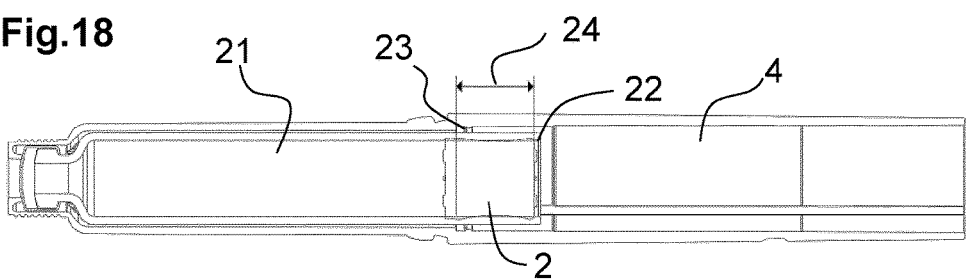
FIG. 18 is a cut-away view of a drug delivery device indicating dimensions to be measured.
Figure 19:
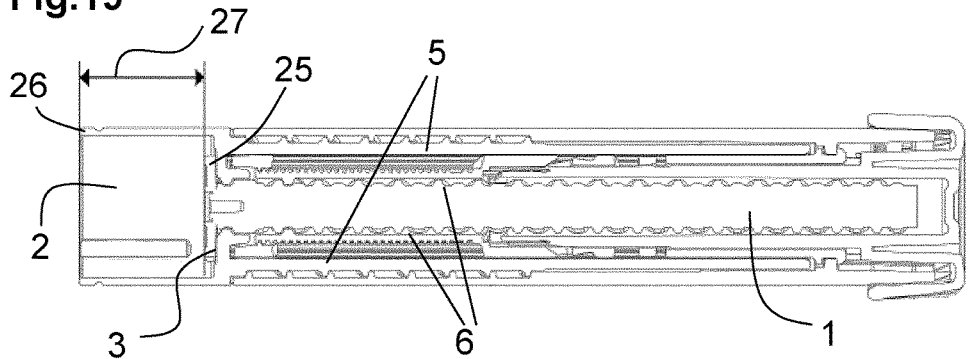
FIG. 19 is a cross section of a drug delivery device indicating dimensions to be measured.

Another method will now be described in conjunction with FIG. 18, which is a cut-away view of a drug delivery device, and with FIG. 19, which is a cross section of a drug delivery device. In this example, with only the cartridge 21 assembled into the outer body 4, the position of the rear surface 22 of the bung 2 facing the piston rod 1 is measured relative to a datum feature on the outer body 4. This datum feature may be the rim 23 of the outer body 4, for example. A distance 24 that may be measured in this manner is indicated in FIG. 18. The position of the front surface 25 of the bearing 3 facing the bung 2 is measured relative to a datum feature on the inner body 5. The latter datum feature may be the rim 26 of the inner body 5, for example. A distance 27 that may be measured in this manner is indicated in FIG. 19. A small force is applied to the piston rod 1 during the measurements to ensure that the backlash in the threaded engagements, particularly in the threads 8, 8', 9, 9', is taken up. If the drive member 6 is present in this stage of the assembly, a biasing force may also be applied to the drive member 6. A calculation is preferably performed to determine the resulting gap between the components if they were assembled in this state. The piston rod 1 is then advanced until the gap has been taken up. This can be achieved either by setting and dispensing an appropriately sized dose, or by rotating the drive member 6 relative to the inner body 5 before finishing the assembly. The drive mechanism can be assembled to the outer body 4 before or after the adjustment has taken place.

Another method will now be described in conjunction with FIG. 20, which is a schematic cross section showing a device and an assembly tool. This method does not require any force, torque or displacement measurement. The essential components including at least the piston rod 1, the inner body 5, the drive member 6 and the dial member 7 are preferably assembled together as a sub-assembly. In this condition the drive member 6 is rotationally fixed to the inner body 5 via the clicker arms 15 and axially fixed to the dial member 7. The piston rod 1 is assembled in a position such that it is sure to make contact with the bung 2 when assembled, allowing for maximum tolerance in the bung position. The sub-assembly is driven into the outer body 4 by applying a force to the dial member 7, which can be effected by an outer part of the assembly tool 20 shown in FIG. 20. This also ensures the dial member 7 is in its initial position, corresponding to zero units dialed, relative to the inner body 5.

The assembly tool 20 comprises a part that is shaped to contact the end face of the drive member 6, biasing it in the direction of the bung 2 relative to the dial member 7. The force applied to the drive member 6 is preferably adapted to be sufficient to make the tapered end of the assembly tool 20 deflect the clicker arms 15 inwards by means of ramped surfaces (cf. FIGS. 9 and 10), so that the clicker arms 15 are disengaged from the inner body 5. The reaction force acting between the drive member 6 and the dial member 7 is equal to this force. Each part of the assembly tool 20 is free to rotate on a bearing in the assembly head.

When the piston rod 1 contacts the bung 2, it will no longer move axially, but will rotate as the inner body 5 moves into the outer body 4. The rotation of the piston rod 1 causes the drive sleeve 6 to rotate as well. As there is a friction between the drive sleeve 6 and the dial sleeve 7, a certain axial force must be applied to the piston rod 1 in order to overcome the frictional torque and to allow the rotation This force effectively pre-loads the bung 2 and stops the axial movement of the piston rod 1 with the rest of the sub-assembly.

After the inner body 5 has been fully inserted into the outer body 4, the assembly tool 20 is removed, and the clicker arms 15 spring outwards. As in the embodiment comprising clicker arms 15 the rest positions of the drive member 6 are restricted to a number of discrete positions defined by features of the inner body 5, the highest accuracy that can be achieved is ±0.5 units for this embodiment, although the accuracy may be different for other embodiments. The rotational position of the drive member 6 can be measured via the assembly tool 20, allowing an operation button to be aligned at the correct angle to finish the assembly.

Figure 20:
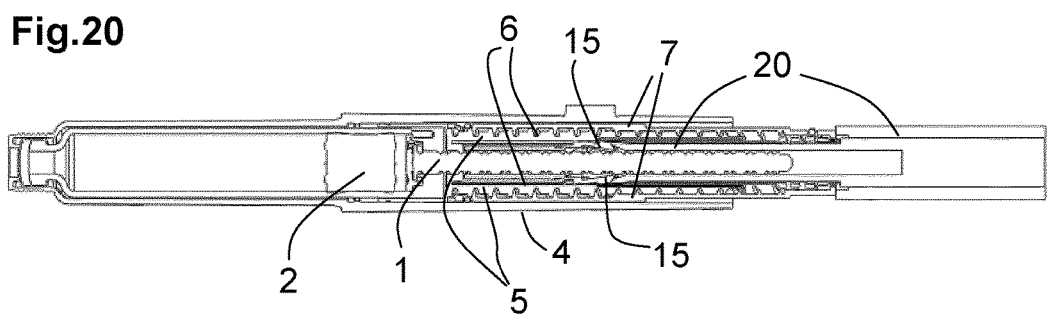
FIG. 20 is a schematic cross section showing a device and an assembly tool.
Figure 21:
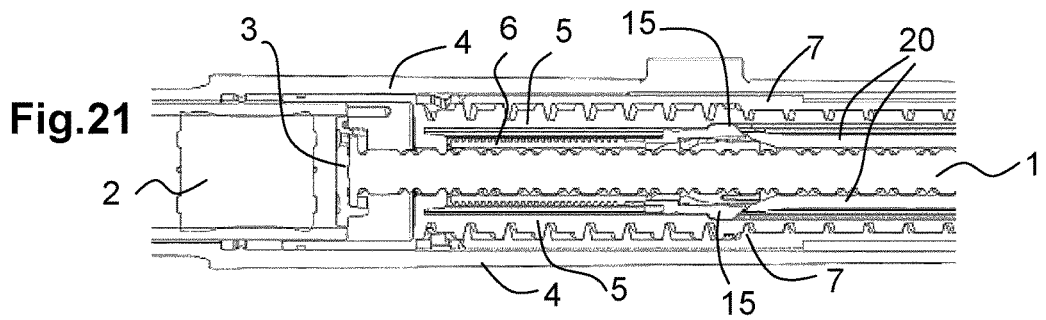
FIG. 21 is a section of the cross section according to FIG. 20 at a starting position.

FIG. 21 is a section of the cross section according to FIG. 20 at a starting position showing the piston rod 1, the bung 2, the bearing 3 of the piston rod 1, the outer body 4, the inner body 5, the drive member 6, the dial member 7, the clicker arms 15, and the assembly tool 20.

Figure 22:
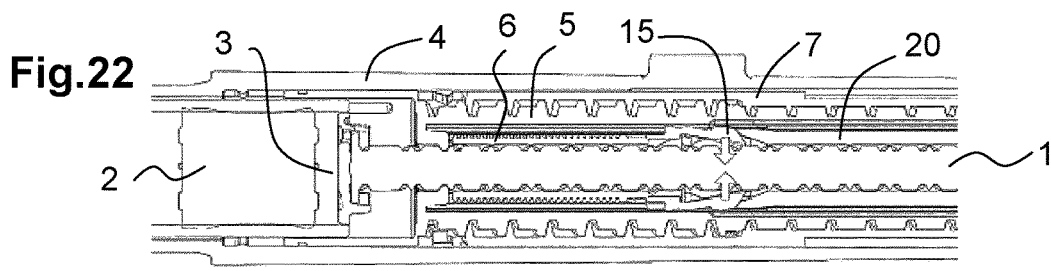
FIG. 22 is a cross section according to FIG. 21 at a later state of assembly.

FIG. 22 shows a cross section according to FIG. 21 for the state in which the assembly tool 20 is driven forwards to a predefined position, forcing the clicker arms 15 inwards, as indicated by the small arrows.

Figure 23:
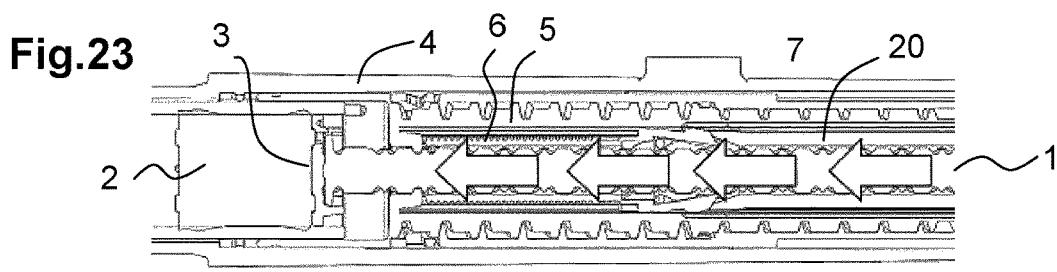
FIG. 23 is a cross section according to FIG. 22 at still a later state of assembly.

FIG. 23 shows a cross section according to FIG. 22 for the state in which a force is applied to the dial member 7, and sub-assembly components move axially, as indicated by the arrows, until contact between the bearing 3 and the bung 2 is achieved.

Figure 24:
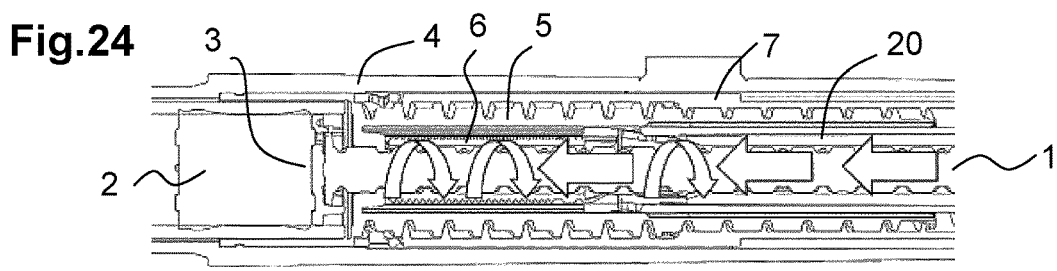
FIG. 24 is a cross section according to FIG. 23 with the bearing contacting the bung.

FIG. 24 shows a cross section according to FIG. 23 for the state in which the bearing 3 contacts the bung 2, and the piston rod 1 can no longer move axially. The inner body 5 continues to move axially, causing the piston rod 1 to rotate, as indicated by the curved arrows. The drive member 6 and the assembly tool 20 move axially and rotationally.

Figure 25:
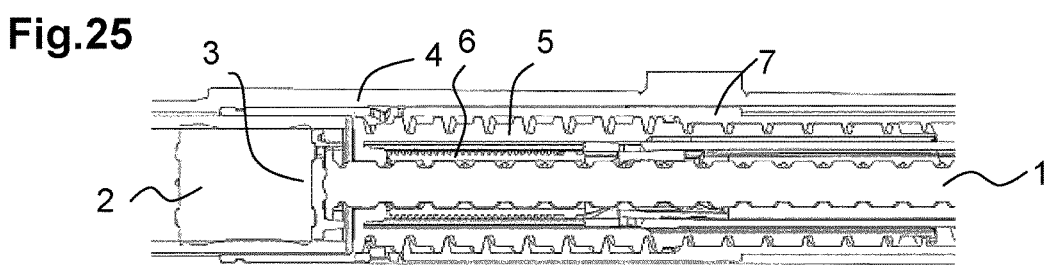
FIG. 25 is a cross section according to FIG. 24 after the removal of the assembly tool.

FIG. 25 shows a cross section according to FIG. 24 for the state in which the inner body 5 is fully assembled into the outer body 4. The assembly tool 20 is removed, allowing the clicker arms 15 to return to their previous positions. The device is now ready for use.

Figure 26:
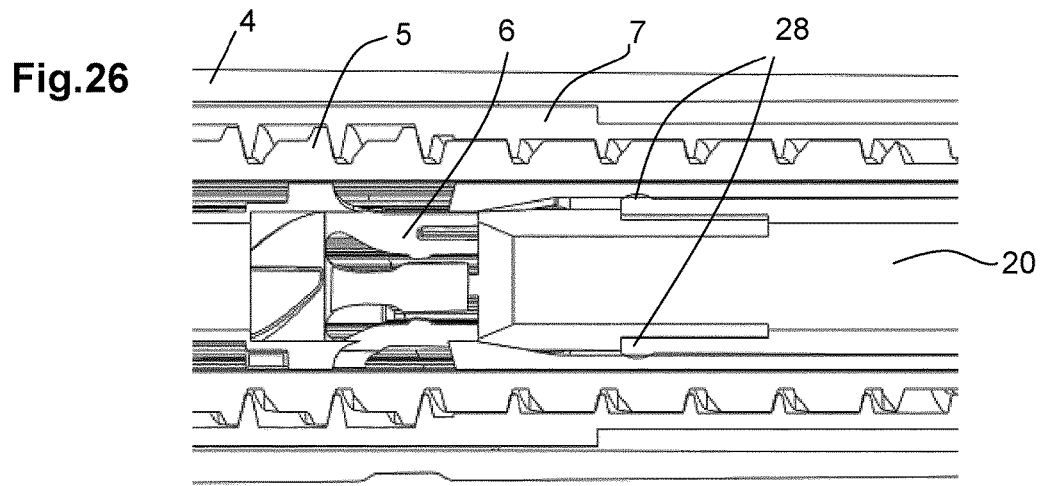
FIG. 26 is a section of the cross section according to FIG. 20 for a further embodiment.

Testing has shown that the preload force applied to the bung 2 must be within a certain range to give a first dose size that is within acceptable limits. With the embodiment described above the force applied to the bung 2 is related to the force required to deflect the clicker arms 15 inwards, potentially giving a bung force that is too high. An additional advantage is obtained if a friction fit between the assembly tool 20 and the drive member 6 is employed, such that the force acting on the clicker arms 15 is in effect generated by the drive member 6. The only force acting externally on the drive member 6 would be the weight of the assembly tool 20 or a controlled applied load. The friction fit may be achieved by friction features added to the assembly tool 20. The cross section of FIG. 26 shows an example of friction features 28 formed by arms, which may be sprung outwards against the inside of the drive member 6, for instance, or detent into features on the drive member 6.

Figure 27:
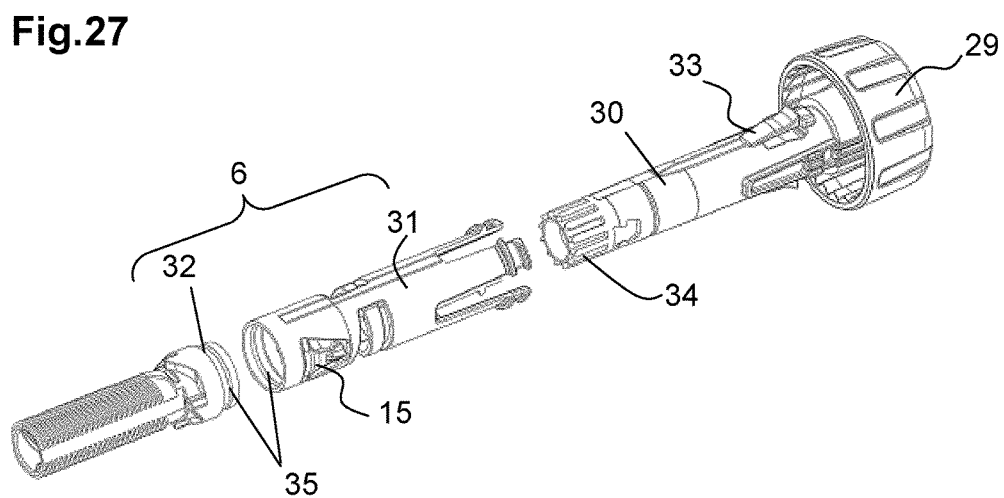
FIG. 27 is an exploded view of parts of a drive mechanism.

A further embodiment and method of assembly will be described in conjunction with FIGS. 27 to 31. FIG. 27 shows an exploded view of an arrangement of a button member 30 comprising an operation button 29, and a drive member 6 comprising a first part 31 and a second part 32. This embodiment does not require any force, torque or displacement measurement for assembly and does not require complex assembly steps. The first part 31 of the drive member 6 is arranged between the second part 32 and the button member 30. The first part 31 and the second part 32 of the drive member 6 are held together axially. This may be achieved by clip features 35. The first part 31 and the second part 32 of the drive member 6 are free to rotate relative to each other. The second part 32 comprises thread features which engage with the piston rod 1. If clicker arms 15 are provided for this embodiment, they are preferably formed in the first part 31.

A first locking feature 33 of the button member 30, which may comprise splines, is engaged with a corresponding feature of the first part 31 of the drive member 6 and rotationally locks the button member 30 with the first part 31. A second locking feature 34 of the button member 30, which may also comprise splines and which may be arranged on the end of the button member 30 facing the drive member 6, is engaged with a corresponding feature of the second part 32 of the drive member 6 and rotationally locks the button member 30 with the second part 32. Both parts 31, 32 of the drive member 6 are therefore rotationally locked to the button member 30 when it is inserted, and these three parts can only rotate simultaneously.

Figure 28:
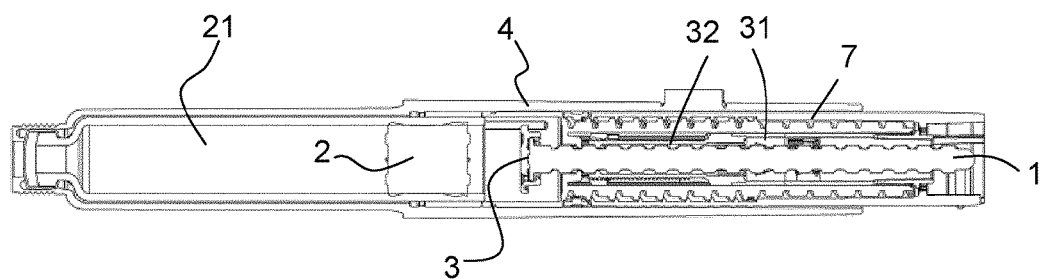
FIG. 28 is a cross section showing a device during assembly for the embodiment according to FIG. 27.

The piston rod 1, the inner body 5, the drive member 6, and the dial member 7 are assembled together as a sub-assembly. FIG. 28 is a cross section of an embodiment comprising the components shown in FIG. 27 in the state when the sub-assembly is inserted into the outer body 4 including a cartridge 21 with the bung 2. In this condition the first part 31 of the drive member 6 is rotationally fixed to the inner body 5 via the clicker arms 15, if provided, and is axially fixed to the dial member 7. Helical movement of the piston rod 1 relative to the inner body 5 will therefore cause axially static rotation of the second part 32 of the drive member 6. The piston rod 1 is assembled in a position such that it is sure to make contact with the bung 2, allowing for maximum tolerance in the bung position. When the piston rod 1 contacts the bung 2 it will be forced helically inwards relative to the inner body 5. This causes rotation of the second part 32 of the drive member 6, but nothing else.

Figure 29:
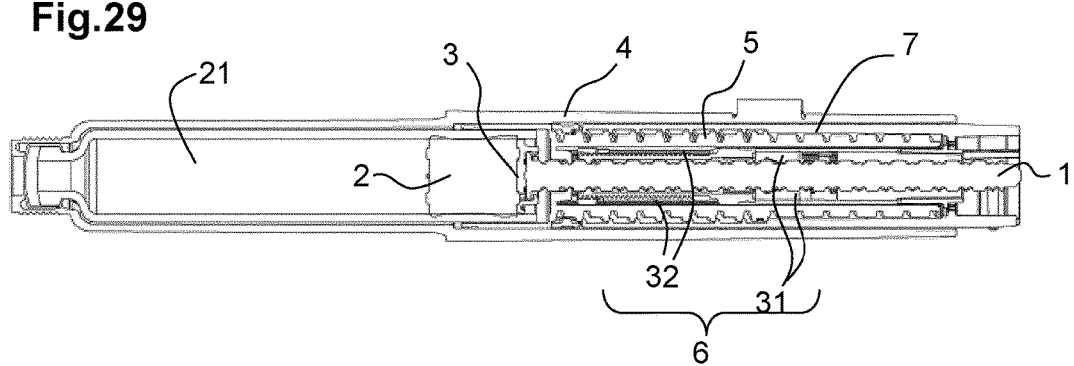
FIG. 29 is a cross section according to FIG. 28 with the bearing contacting the bung.

FIG. 29 is a cross section according to FIG. 28 for the state in which the bearing 3 contacts the bung 2. The piston rod 1 moves helically relative to the inner body 5. The second part 32 of the drive member 6 rotates relative to the inner body 5.

Figure 30:
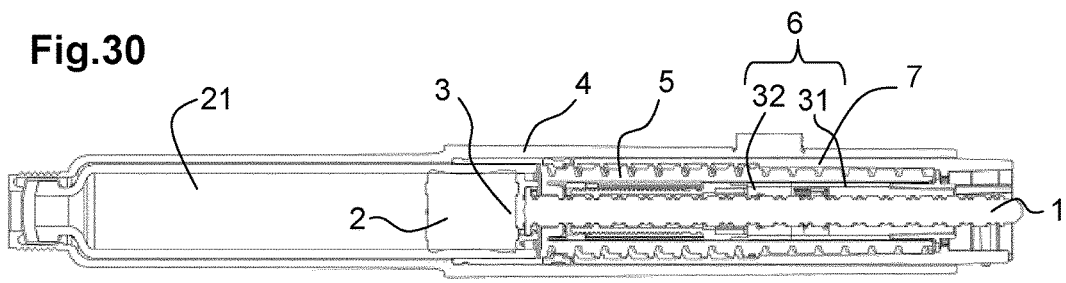
FIG. 30 is a cross section according to FIG. 29 at a later state of assembly.
Figure 31:
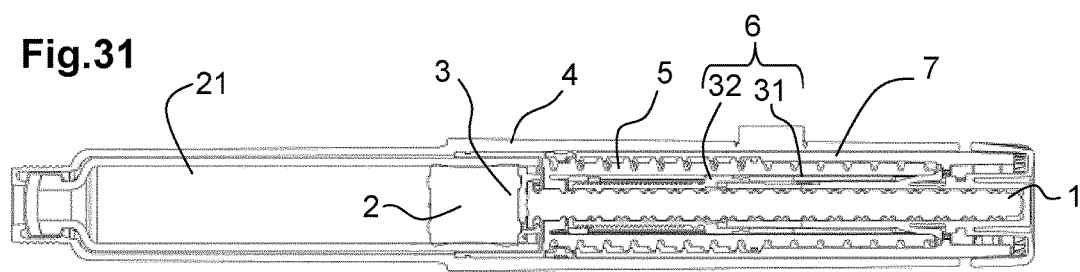
FIG. 31 is a cross section according to FIG. 30 after assembly.

FIG. 30 is a cross section according to FIG. 29 for a later state in which the inner body 5 is fully inserted into the outer body 4. Then the button member 30 is assembled to the device and becomes rotationally locked to both parts 31, 32 of the drive member 6. This finishes the assembly and renders the device as shown in the cross section of FIG. 31.

If the second locking feature 34 of the button member 30 comprises a discrete number of splines, the second part 32 of the drive member 6 is forced into a rotational position that allows the splines to engage. This rotational position also defines the axial position of the piston rod 1, which is therefore forced into one of a number of discrete axial positions after the device is fully assembled. Thus there is a certain error on the position of the piston rod 1 relative to the bung 2. This embodiment is illustrated in FIG. 27 with the second locking feature 34 comprising twelve splines, corresponding to a resolution of one unit. It is however more favourable to have twenty-four splines to match the resolution of ±0.5 units of the preceding embodiments, although any number of splines could be incorporated.

Figure 32:
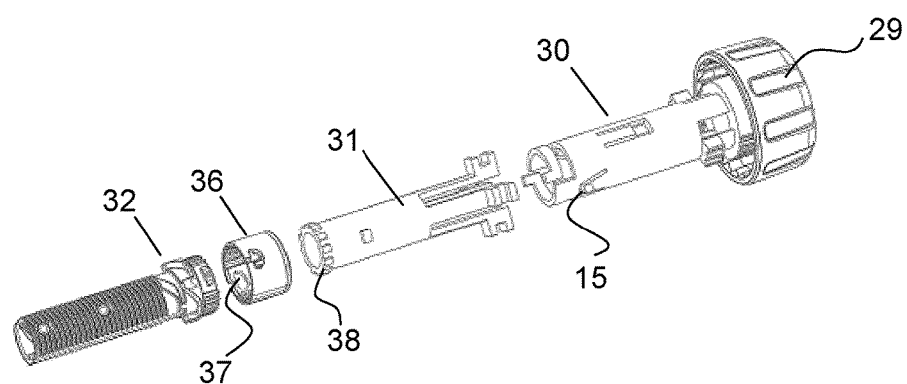
FIG. 32 is an exploded view of parts of a further embodiment of a drive mechanism.

A further embodiment and method of assembly will be described in conjunction with FIGS. 32 to 36. FIG. 32 shows an exploded view of an arrangement of a button member 30 comprising an operation button 29, and a drive member 6 comprising a first part 31, a second part 32 and a coupler 36. This embodiment does not require any force, torque or displacement measurement for assembly. The first part 31 of the drive member 6 is arranged between the second part 32 and the button member 30. The coupler 36 is fastened to the second part 32 of the drive member 6. This may be achieved by clip features 37. The second part 32 comprises thread features which engage with the piston rod 1. If a clicker arm 15 is provided for this embodiment, it is preferably formed in the button member 30, but there may instead be a clicker arm on the drive member 6 or clicker arms on the drive member 6 and on the button member 30. The coupler 36 and the first part 31 of the drive member 6 comprise corresponding locking features 38, which may be clutch teeth, for example. These locking features 38 engage when the second part 32 is arranged adjacent to the first part 31 and rotationally lock the second part 32 including the coupler 36 and the first part 31 of the drive member 6.

Figure 33:
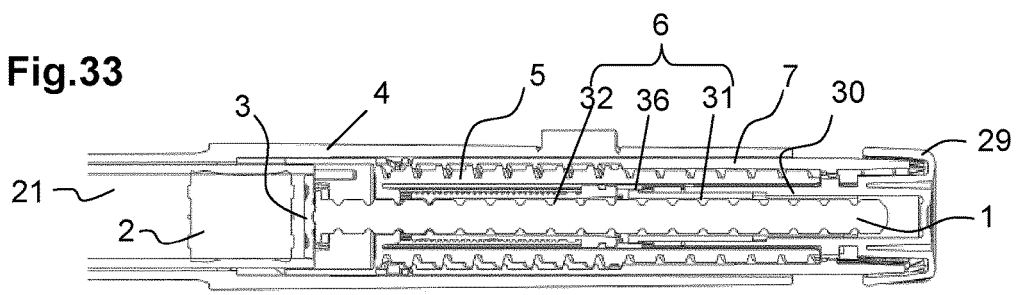
FIG. 33 is a cross section showing a device during assembly for the embodiment according to FIG. 32.

The piston rod 1, the inner body 5, the drive member 6, and the dial member 7 are assembled together as a sub-assembly. FIG. 33 is a cross section of an embodiment comprising the components shown in FIG. 32 in the state when the sub-assembly is inserted into the outer body 4 including a cartridge 21 with the bung 2. In this condition the button member 30 is mounted, and the first part 31 of the drive member 6 is rotationally locked to the inner body 5 via the clicker arms 15 on the button member 30 and axially locked to the dial member 7. The piston rod 1 is assembled in a position such that it is sure to make contact with the bung 2, allowing for maximum tolerance in the bung position. When the piston rod 1 contacts the bung 2 it will be forced helically inwards relative to the inner body 5. This causes the second part 32 of the drive member 6 to move axially relative to the first part 31, until the clutch formed by the coupler 36 disengages and the second part 32 is free to rotate. The second part 32 continues to rotate as the sub-assembly is inserted into the outer body 4.

Figure 34:
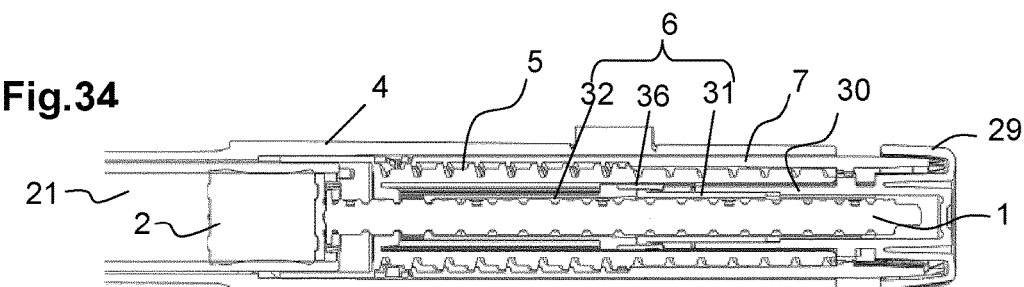
FIG. 34 is a cross section according to FIG. 33 with the bearing contacting the bung.

FIG. 34 is a cross section according to FIG. 33 for the state in which the bearing 3 contacts the bung 2. The piston rod 1 moves helically relative to the inner body 5. The second part 32 of the drive member 6 rotates relative to the inner body 5.

Figure 35:
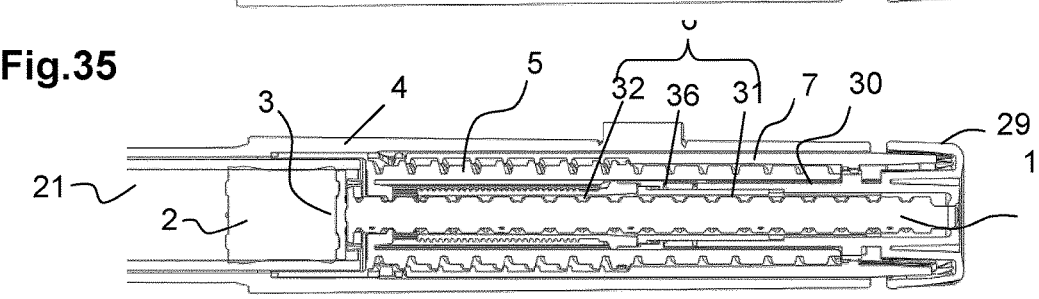
FIG. 35 is a cross section according to FIG. 34 at a later state of assembly.

FIG. 35 is a cross section according to FIG. 34 for a later state in which the inner body 5 is fully inserted into the outer body 4, and the bearing 3 is in contact with the bung 2. The clutch features formed by the coupler 36 connecting the first part 31 and the second part 32 of the drive member 6 are still disengaged. To allow them to re-engage the first part 31 must move away from the second part 32. In this embodiment this may be achieved by moving the inner body 5 and simultaneously the first part 31 away from the bung 2. The inner body 5 is rotated, and a ramp feature (ramp feature 40 shown in FIG. 37, for example), which is provided for this purpose, forces the inner body 5 to move axially. When the rotation is complete, a clip feature (clip feature 39 shown in FIG. 37, for example) locks the inner body 5 to the outer body 4 rotationally and axially. The first part 31 of the drive member 6 has now moved a sufficient distance to allow the clutch teeth formed by the locking features 38 to re-engage, rotationally locking the first part 31 and the second part 32. This finishes the assembly and renders the device as shown in the cross section of FIG. 36.

If the locking feature 38 of the coupler 36 and the first part 31 of the drive member 6 comprises a discrete number of splines or clutch teeth, the second part 32 of the drive member 6 is forced into a rotational position that allows these features to engage. This rotational position also defines the axial position of the piston rod 1, which is therefore forced into one of a number of discrete axial positions after the device is fully assembled. Thus there is a certain error on the position of the piston rod 1 relative to the bung 2. This embodiment is illustrated in FIG. 32 with the locking feature 38 comprising twelve teeth, corresponding to a resolution of one unit. It is however more favourable to have twenty-four teeth to match the resolution of ±0.5 units of the preceding embodiments, although any number of splines or clutch teeth could be incorporated.

Figure 36:
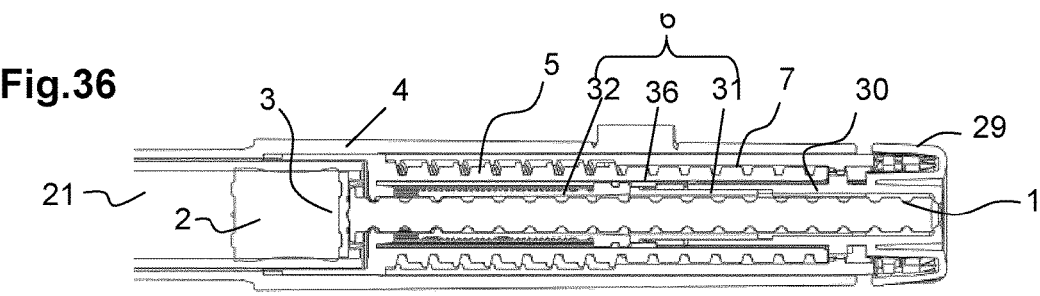
FIG. 36 is a cross section according to FIG. 35 after assembly.
Figure 37:
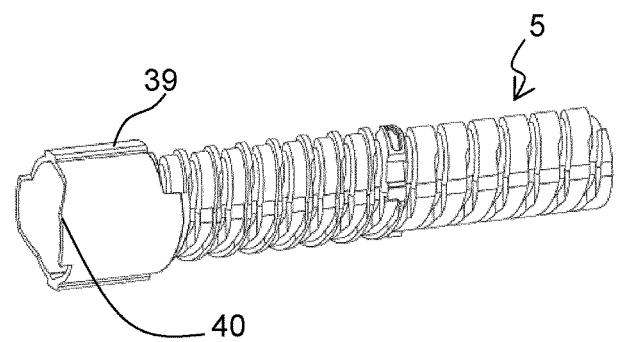
FIG. 37 shows an inner body of an embodiment according to FIG. 36.

FIG. 37 shows an inner body 5 of an embodiment according to FIG. 36. The clip feature 39 is used to lock the inner body 5 to the outer body 4 rotationally and axially when the assembly is finished. The ramp feature 40, together with a corresponding ramp feature of the outer body 4 (ramp feature 42 in FIG. 38, for example), generates an axial movement of the inner body 5 when it is rotated relative to the outer body 4.

Figure 38:
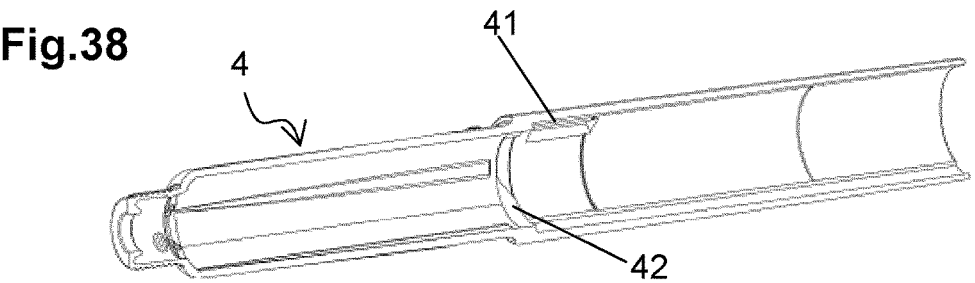
FIG. 38 shows an outer body of an embodiment according to FIG. 36.

FIG. 38 shows an outer body 4 of an embodiment according to FIG. 36. The clip feature 41 is used to lock the inner body 5 to the outer body 4 rotationally and axially when the assembly is finished. The ramp feature 42, together with a corresponding ramp feature of the outer body 4 (ramp feature 40 in FIG. 37, for example), generates an axial movement of the inner body 5 when it is rotated relative to the outer body 4.

Figure 39:
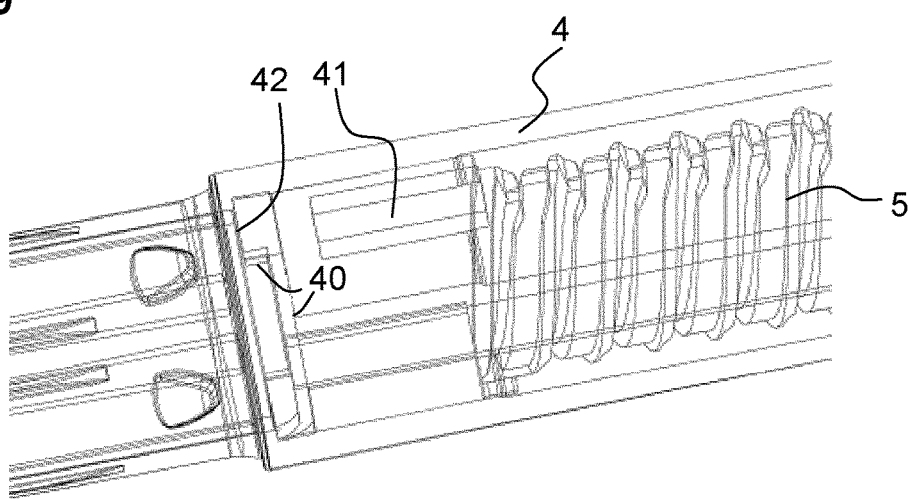
FIG. 39 shows a semitransparent view of an embodiment according to FIG. 36 after an axial assembly stage.

FIG. 39 shows a semitransparent view of an embodiment according to FIG. 36 after an axial assembly stage. The inner body 5 comprising a ramp feature 40 is inserted in the outer body 4 comprising a clip feature 41 and a ramp feature 42.

Figure 40:
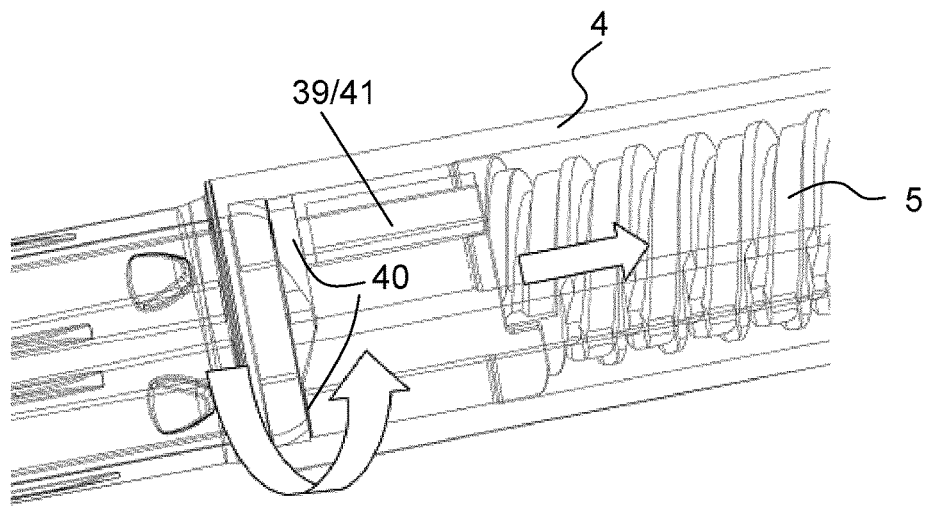
FIG. 40 shows a semitransparent view of an embodiment according to FIG. 36 after rotation of the inner body.

FIG. 40 shows a semitransparent view according to FIG. 39 after a rotation of the inner body 5 relative to the outer body 4, indicated by the curved arrow. During the rotation of the inner body 5, the ramp features 40, 42 generate an axial movement of the inner body 5 away from the bung 2, indicated by the straight arrow. After the rotation, the clip features 39, 41 are engaged and lock the inner body 5 axially and rotationally to the outer body 4. It is also possible to fasten the outer body 4 and the inner body 5 by laser beam welding or the like, in order to fix the positions of these elements after a relative movement.

Types of drug delivery devices include reusable devices, which are refilled, and so-called disposable devices, which are not refilled and are disposed of when empty. This invention is particularly advantageous for disposable devices, because they can be provided ready for use by the methods described above, and as no new cartridge will be inserted, there is no future need either for a priming of the device.

The invention claimed is:

1. A drug delivery device, comprising:
a piston rod arrangement in an assembled state before the first use, comprising
a piston rod,
a bung,
a body member, the piston rod being threadedly engaged with the body member,
a drive member threadedly engaged with the piston rod and provided to advance the piston rod, the drive member having a first part and a second part, wherein the second part is threadedly engaged with the piston rod,
a coupler fastened to the second part, the first part and the second part being releasably rotationally locked by the coupler,
a ramp feature provided on the body member, and
a further body member provided with a corresponding ramp feature, the ramp features configured to transform a relative rotation of the body member and the further body member into a relative shift,
the drive member being movable relative to the body member, a mechanism being provided for defining unit steps of movement of the drive member and corresponding unit steps of movement of the piston rod, wherein
the piston rod is arranged in contact with the bung or at a distance from the bung that is less than a distance of one corresponding unit step of movement.

2. The drug delivery device according to claim 1, wherein the piston rod is arranged at a distance from the bung that is less than a distance of half a corresponding unit step of movement.

3. The drug delivery device according to claim 1, wherein the mechanism defining unit steps of movement is formed by a feature acting between the body member and the drive member.

4. The drug delivery device according to claim 1, further comprising:
a dial member coupled with the drive member, wherein the mechanism defining unit steps of movement is provided by a feature formed on the body member and on the dial member.

5. The drug delivery device according to claim 1, wherein the first part and the second part of the drive member are coupled in such a manner that the first part and the second part can rotate relative to one another.

6. The drug delivery device according to claim 5, further comprising:
a button member comprising an operation button, the first part of the drive member being arranged between the second part and the button member, and
a first locking feature of the button member, the first locking feature being engaged with a corresponding feature of the first part of the drive member, the first locking feature rotationally locking the button member with the first part.

7. The drug delivery device according to claim 6, further comprising:
a second locking feature of the button member, the second locking feature being engaged with a corresponding feature of the second part of the drive member, the second locking feature rotationally locking the button member with the second part.

8. The drug delivery device according to claim 1, further comprising:
threads threadedly engaging the piston rod with the body member, and
further threads threadedly engaging the piston rod with the drive member, wherein
the thread of the body member has an area of contact on the body member and
the thread of the drive member has an area of contact on the drive member, the areas of contact being in contact with the piston rod in such a manner that no backlash between the drive member, the piston rod and the body member interferes with an advancement of the piston rod by the drive member or that a backlash between the drive member, the piston rod and the body member is so small that the backlash only causes a reduction of the advancement of the piston rod by less than a distance of one corresponding unit step of movement.

9. The drug delivery device according to claim 1, wherein the drug delivery device is a disposable device.

10. The drug delivery device according to claim 1, wherein the drug delivery device is a variable dose device.

11. A method for eliminating a clearance of a piston rod for drug delivery devices, comprising the steps of:
assembling a piston rod, a bung, and a drive member provided for generating a movement of the piston rod in a body member in such a manner that
the bung is stationary with respect to the body member, and
the piston rod is threadedly engaged with the body member and with the drive member,
wherein either
a) the piston rod is advanced with respect to the body member towards the bung, until the piston rod is stopped by the bung, the drive member is rotated until the piston rod begins to advance again, and the drive member is then stopped, and the piston rod is fixed at or near the position obtained, or b) a frictional force is used to generate a torque acting between the body member and the drive member, the body member is shifted in the direction towards the bung, driving the piston rod into contact with the bung and generating a rotation of the piston rod, which causes a rotation of the drive member against the action of the torque, and the piston rod is driven into contact with the bung against the action of said torque by a force loading the bung with a resilient force.

12. The method of claim 11, wherein either a) the piston rod is advanced with respect to the body member towards the bung, until the piston rod is stopped by the bung, the drive member is rotated thus rotating the piston rod by the threaded engagement of the piston rod with the drive member, until the piston rod begins to advance again relative to the body member by the threaded engagement of the piston rod with the body member; and the drive member is then stopped, and the piston rod is fixed at or near the position obtained, or b) a frictional force is provided acting between the body member and the drive member, the body member is shifted in the direction towards the bung, driving the piston rod into contact with the bung and generating a rotation of the piston rod, by the threaded engagement of the piston rod with the body member, which causes a rotation of the drive member against a torque generated by said frictional force, and the piston rod is driven into contact with the bung against the action of said torque by a force loading the bung with a resilient force.

13. The method of claim 11, wherein the drive member is rotated in increments of unit steps of movement generating a corresponding advancement of the piston rod as long as the piston rod is free to advance, and the drive member is stopped at the end of a unit step of movement that is not accompanied by a corresponding advancement of the piston rod.

14. The method of claim 11, wherein a backlash between the piston rod, the drive member and the body member is determined beforehand, the drive member is rotated in increments of unit steps of movement generating a corresponding advancement of the piston rod as long as the piston rod is free to advance, and when a unit step of movement is not accompanied by a corresponding advancement of the piston rod, the drive member is further rotated until the backlash is removed.

15. The method of claim 11, wherein the drive member is rotated in increments of unit steps of movement generating a corresponding advancement of the piston rod as long as the piston rod is free to advance, after an increment that is not accompanied by a corresponding advancement of the piston rod, the drive member is further rotated until the end of a first increment that is again accompanied by a corresponding advancement of the piston rod is reached, and the drive member is rotated back by one unit step or by two unit steps, depending on the preceding advancement of the piston rod.

16. The method of claim 11, wherein the advancement of the piston rod is determined by a measurement of a torque reacting on the drive member.

* * * * *